(12) United States Patent
Jacobs et al.

(10) Patent No.: US 8,810,388 B2
(45) Date of Patent: Aug. 19, 2014

(54) POSITION TRACKING AND MOBILITY ASSESSMENT SYSTEM

(76) Inventors: Peter G. Jacobs, Portland, OR (US); Eric A. Wan, Portland, OR (US); Anindya S. Paul, Portland, OR (US)

( * ) Notice: Subject to any disclaimer, the term of this patent is extended or adjusted under 35 U.S.C. 154(b) by 0 days.

(21) Appl. No.: 13/403,647

(22) Filed: Feb. 23, 2012

(65) Prior Publication Data
US 2013/0141233 A1    Jun. 6, 2013

Related U.S. Application Data

(60) Provisional application No. 61/445,619, filed on Feb. 23, 2011.

(51) Int. Cl.
*G08B 19/00*    (2006.01)

(52) U.S. Cl.
USPC ....... 340/521; 340/539.11; 340/540; 600/300

(58) Field of Classification Search
None
See application file for complete search history.

(56) References Cited

U.S. PATENT DOCUMENTS

| | | | |
|---|---|---|---|
| 2006/0206011 A1* | 9/2006 | Higgins et al. | 600/300 |
| 2010/0298656 A1* | 11/2010 | McCombie et al. | 600/301 |

* cited by examiner

*Primary Examiner* — Hai Phan
*Assistant Examiner* — Ojiako Nwugo
(74) *Attorney, Agent, or Firm* — McNeely, Hare & War, LLP; William D. Hare, Esq.

(57) ABSTRACT

The invention relates to a system and method for monitoring the location, movement and health of one or more individuals within an environment by a monitoring individual, such as a care giver. The system used includes optional monitoring devices including a wireless transceiver, access point devices including a wireless transceiver, a hub access point device including a wireless transceiver, and a local computing device. The system is programmed such that it has the capability to operate with or without the measure of time of flight value from the optional monitoring devices such that the system has the capability of monitoring the location, movement and health of an individual whether or not the individual is wearing the monitoring device.

20 Claims, 13 Drawing Sheets

Figure 10: Tag-based tracking results using TOF transceivers and SPKS tracking algorithm. The dashed line is the true walking path and the solid line is the predicted walking path. The subject entered the facility though a door at the start of the walk and exited at the end.

POSITION TRACKING AND MOBILITY ASSESSMENT SYSTEM

CROSS-REFERENCE TO RELATED APPLICATIONS

This application is a nonprovisional of, and claims priority to U.S. provisional patent application No. 61/445,619, filed on Feb. 23, 2011, the contents of which are incorporated herein in their entirety by reference.

TECHNICAL FIELD

The field of the invention generally relates to a set of devices, a method, and a software system that monitors and assesses a patient's position and mobility in an indoor living environment that can be used to determine the health status of a person living independently in their home or in an assisted living facility. The invention also includes a method and software system that can electronically alert family, friends, and/or a caregiver if the system determines that the patient requires medical assistance.

BACKGROUND

The system is designed, in part, to address a problem of a rapidly aging population in the United States that is placing a significant financial and logistical burden on the health care system, families, elderly individuals and older adults. According to a Congress of the United States Congressional Budget Office report entitled "Financing Long-term Care for the Elderly," the cost of long-term healthcare services for older adults in the United States who suffer from physical and cognitive effects of aging was $135 billion U.S. in 2004. However, many of these older adults and individuals would prefer to remain in their homes, even as their health deteriorates, if they could be assured that someone would know when they suffered a health emergency so that they could receive medical care in a timely manner.

Currently, there are limited options for older adults suffering from health complications, illness, or the general effects of aging to live independently in their home without risk of experiencing a medical emergency that goes undiscovered for a potentially lengthy period of time. Many older adults that attempt to live independently suffer medical emergencies such as a fall, stroke, epileptic seizure, or diabetic coma. These medical emergencies are only discovered when a family member, friend, neighbor, caregiver or other individual calls and receives no answer, or physically visits the person and determines that the person has suffered a medical emergency. In many cases, a lengthy time between the start of the medical emergency and its discovery by a third party can result in trauma, severe and irreversible health damage, or even death. Furthermore, immediate discovery of a medical emergency is critical with many medical conditions, such as a stroke or heart attack, where minimizing the time between when the medical event occurs and the patient receives medical care can significantly impact the long-term health outcome as well as the associated costs of care.

To address these concerns, many older adults spend money out-of-pocket or use their health insurance to obtain in-home care. The caregiver may live in the home with the patient or may visit periodically to ensure the patient is okay. Because many older adults only need medical care if a medical emergency occurs, having a caregiver present to this degree is often beyond what the patient needs and impinges on their desire for privacy and independence.

Alternatively, many older adults move out of their homes into assisted living facilities where medical care is readily available should they need it. Frequently the older adult would prefer to remain in his or her own home, but due to concerns of burdening friends and family members with checking on them, or of suffering a medical emergency that goes undiscovered, chooses to move to an assisted living facility.

In either situation, there is a waste of resources by, and a loss of independence for, the older adult: either the patient is spending out-of-pocket or health insurance resources to pay a healthcare provider to be in the patient's home or the patient is spending these resources to stay in a typically expensive assisted living facility. In addition, the patient must compromise his or her desire for independence when a caregiver must live in or visit the home, or when the patient must leave his or her home and move into an assisted living facility, a family member's home, or some other living situation that provides some level of home monitoring.

Likewise, family members and friends may make sacrifices of time, money, and convenience to check in on the patient. They may need to take the time to periodically visit the older adult. They may also pay a caregiver to periodically visit the older adult or live in the patient's home, they may pay to house the older adult in an assisted living facility, or they may have the patient move into their home.

A final alternative is that the older adult chooses to remain in his or her home, with no third party individual checking in on or living with the person. In such cases, if a medical emergency occurs, it is likely that the emergency will not be discovered until significant health damage or death has occurred.

In addition, many facilities for the elderly, such as adult foster care homes and assisted living facilities, have multiple people that require monitoring. In such cases, the staff person or people responsible for the care of the older adults cannot monitor all of them 24 hours a day. Some facilities even offer a tiered or graduated structure for care in which the patient lives in his or her own home or apartment at the facility, only moving to living accommodations with more frequent monitoring when health issues warrant that higher level of monitoring and access to care. In these cases, medical care is available within the community, and the medical and facility staff may periodically check in on the patient. However, due to high patient-to-staff ratios, residents cannot be continuously monitored. This means that in some cases, they suffer a medical emergency with significant delay before someone discovers it. During this period of time, the older person's medical condition may worsen or permanent damage to the individual's health may occur.

Elderly adults that suffer from physical and cognitive effects of aging can live independently in their home much longer if a third party entity could monitor a patient remotely and receive an alert immediately if a medical emergency has occurred. Due to the high patient-to-staff ratios at assisted living facilities, the staff working in these facilities need assistance with monitoring older adults for medical emergencies.

The inventors have developed a set of devices, methods and a software system that can be used in an indoor environment, such as a home, apartment, hospital, or assisted living facility, to unobtrusively monitor a patient's movement patterns, detect changes over time, and thereby determine if the patient may have suffered a medical emergency and to alert one or more third parties that a medical emergency has likely occurred. The system also enables one or more third parties to unobtrusively conduct real-time monitoring of one or more patient's position and mobility within an indoor environment. The system uses this position and mobility information as a metric for assessing the person's health status over time and comparing current mobility metrics with long-term trends.

The devices, methods, and software system disclosed herein will be useful in unobtrusively monitoring multiple older adults living in a multi-patient facility, such as an adult foster care home, assisted living facility or retirement community with graduated levels of residence options based on the level of required monitoring and care. In such cases, the person responsible for the resident in the facility may need to monitor several residents who may be in separate rooms in the home. For these staff members, the ability to receive alerts immediately when a medical emergency occurs can enable the staff person to provide immediate medical care or ensure the elderly patient or resident receives immediate access to medical care from a medical provider.

The invention presented herein is a valuable component for enabling older adults to live independently longer. The invention is designed to be a state-of-the-art mobility and health assessment technology that keeps track of location and movement patterns of a person within their home and notifies the older person, friends, family, and/or health care professionals if there is a change in the person's health as assessed based on changes in these movement patterns and activities of daily living. The invention will enable an older adult to live independently within their home or in an assisted living facility without fear that an emergency event might happen without anyone being aware that such an emergency has occurred. The invention will provide peace of mind to these older persons' families and friends who worry about their well-being. The invention will also be of significant benefit to researchers who monitor mobility in older populations during clinical trials for assessing the effectiveness of drugs, surgical procedures, and other treatments for illness in older people.

The invention represents a major leap forward in health monitoring for the elderly due to several key innovations which make the invention the most accurate and reliable method for monitoring mobility and health of a person non-invasively within their home. The invention consists of three modes of operation for performing mobility estimation: 1) a tag-based mode of operation which requires the older adult being monitored to wear a tag on their wrist, ankle, or around their belt, or elsewhere on their body or clothing; 2) an unobtrusive, passive, tag-free position estimation mode of operation which requires no compliance by the older adult being monitored for the case where the older person forgets or chooses not to wear the tag; and 3) a combination of the two above modes of operation whereby mobility is estimated based on a tag-based mobility estimation mode of operation and a tag free mobility estimation mode of operation.

The tag-based mode of operation (see FIG. 4 for illustration of tag, access-points, and hub), designed using time-of-flight wireless radio transceivers, inertial sensors (3-axis accelerometers and gyroscopes), and Bayesian tracking algorithms, will provide accurate sub-meter location and walking speed, detailed movement patterns, derived activities of daily living (bathroom trips, meals, etc.), and information on gait and falls. The tag-free mode of operation does not require a tag to be worn and instead uses advanced classification algorithms that evaluate disruptions in radio frequency (RF) signals between wall-mounted access points as a person walks freely through their home. The tag-free mode can estimate locations within 2-3 meters of accuracy, assess whether multiple people are in a room (assessing social interaction), and potentially indicate falls; this technology avoids privacy issues with alternative video based surveillance, and far supersedes current tag-free position estimators such as those based on infrared motion sensors. As noted above, the invention may be based on using the tag-based mode, the tag-free mode, or a combination of the two.

The inventions described herein represent a major advance in elder care monitoring because they deliver superior tag-based and tag-free mobility assessment and tracking in an easy-to-use and easy-to-install system that is affordable. The inventions have the potential to become the standard of care for 1) enabling older adults to live independently within their own homes for a longer period of time, 2) improving assisted living care for older adults living within care facilities, and 3) delivering superior mobility metrics for research groups who are assessing affects of drugs, surgery, and other therapies on mobility in clinical trials.

Over the last decade, the inventors and their colleagues have installed and evaluated many tracking and in-home health monitoring systems, and have developed approaches for gathering such data unobtrusively. For the most part these methods have allowed at best room-level tracking and are insufficient for identifying key instrumental activities of daily living. While the global positioning system (GPS) has provided standardization for ubiquitous outdoor localization, such systems do not exist indoors. Tags based on RFID, IR, or ultrasound, developed by such companies as Inlocality, Radianse, Awarepoint, and Sonitor, are marketed directly to the healthcare profession for hospital applications, but provide only room level localization at best and are inadequate for extracting activities of daily living (ADL) or other aspects of mobility. A number of companies (e.g. Ekahau Inc, Home-Free Systems) have released tracking tags based on Receiver Signal Strength Indicator (RSSI) positioning using 802.11 standard Wi-Fi routers that purport to achieve localization accuracy of a few meters. In practice, these systems are difficult to calibrate, have poor sample rates and battery life, are plagued by interference issues, and in general exhibit poor performance as observed in our own studies.

A newer approach called ultra-wideband technology (UWB) uses spread-spectrum coding to implement time-difference-of-arrival (TDOA) from a small tag and multiple proprietary based stations. UWB allows for very accurate localization; however, existing commercial systems (e.g. Ubisense, Thales, and RoundTrip), are extremely costly, exceeding tens of thousands of dollars for installation of the base stations. The proprietary base stations are also large, require special wiring, and as such are just not appropriate for most in-home monitoring applications. The selection of technologies for unobtrusive tag-free tracking is even more limited. Due to privacy issues, video based tracking is not an option for most in-home monitoring applications. Simple binary Infra-red (IR) motion detectors may be used to determine region level location (e.g., X-10 IR motion sensors, Versa), but again do not provide accurate activity and mobility information and have issues when more than one individual are in the living space. Additional resolution is possible with arrays of sensors. Mitsubishi Electric Research Laboratories, for example, has a prototype system that requires over 200 IR sensors to be installed in the ceiling of a large office building.

The inventors have experimented with using small linear arrays of IR motion sensors to extract walking speed along a hallway. In general, such arrays are difficult and costly to install. Contact switches may also be placed in doors, beds, or toilets, to help provide localization. The inventors have evaluated many of these systems and all off-the-shelf positioning tracking devices have been found to be unreliable, inaccurate, not scalable, and unable to extract fine details of mobility necessary for meeting the inventors' needs. In one study, use of commercial tag based systems were abandoned because they 1) failed to accurately track 3-d position of the older persons within their homes and 2) because the ongoing maintenance, calibration, and service of these systems proved to be too costly and resource intensive to continue using them. Furthermore, no system currently exists that can provide both position tracking and extraction of other aspects of mobility and health status. The lack of an existing system meeting the needs identified by the inventors has been a primary driver in why the inventions disclosed herein have been designed to meet the needs of the aging population.

This invention addresses many of the shortcomings of existing tracking and monitoring solutions. The invention moves beyond simple passive monitoring of location with the ultimate ability to assess an older person's health based on changes to daily mobility patterns as they move throughout their living environment. Of course, it should be understood that the system may be used in other applications as well, beyond older individuals. For example, people with conditions that impair their movement, such as multiple sclerosis, may enhance their ability to live alone by using one or more of the systems disclosed herein.

As described below, multiple key innovations distinguish the inventions described herein from existing tracking methodologies and systems. Five such innovations are described below. It should be understood that the systems described herein may be based on one or more of these five innovations. Such systems can consist of any one or more of these innovations, consist essentially of any one or more of these innovations, or include any one or more of these innovations.

Innovation 1: Highest accuracy integrated navigation solution that combines Bayesian estimation algorithms with time-of-flight sensors and inertial measurement sensors (accelerometer and gyroscope) to achieve multi-scale tracking capabilities.

The invention achieves the most accurate tag-based tracking performance possible by combining time-of-flight (TOF) ranging sensors and inertial measurement sensors with the most technically advanced Bayesian tracking algorithms currently available. By integrating the inventors' Bayesian state estimation algorithms based on sigma point Kalman filtering (SPKF) with TOF ranging sensors, position tracking accuracy as high as 0.55 meters has been demonstrated which is critical for using mobility as an assessment of health status and changes in activities of daily living. This accuracy is 4 times better than off-the-shelf solutions which use the same hardware but inferior tracking algorithms. Although accuracy to 0.55 meters has been attained, accuracy to 0.6, 0.7, 0.8, 0.9, 1.0, 1.5, 2.0 meters also can be used if desired for various reasons, e.g., cost of system. Therefore the invention should be understood to include a wide range of position tracking accuracies.

The invention also incorporates an inertial measurement unit (IMU) including 3-axis accelerometers and gyroscopes into the design, which in combination with SPKF enables even further increase in tracking performance. The IMU in combination with TOF metrics enables accurate high-bandwidth 3D trajectory estimates with better than centimeter (relative) precision for monitoring precise movement patterns (e.g., gait features and falls). This two-scale performance capability (grosser level using TOF and more precise using TOF plus IMU) is unavailable in all commercial indoor tracking systems and will enable the invention to be used in a far broader array of mobility monitoring and health assessment applications.

Innovation 2: Truly non-obtrusive (i.e., no video monitoring) tag-free tracking for situations when an individual declines or forgets to wear their tag.

While the superior accuracy of this invention's tag-based position monitoring technology is a major innovation, seniors (especially those with cognitive decline) cannot always be relied upon to wear their tag. In addition, many healthy older adults would simply prefer not to have to wear any device. This is why the inventor's tag-free tracking solution is another primary innovation of this invention. The tag-free tracking method is based on the principle that radio frequency (RF) energy between two or more RF transceivers reflect and absorb differently depending on where a person is located within that room. The same wall-mounted access points and hub used in the tag-based tracking mode are used in tag-free mode; however, no tag is required; the older person is not required to wear anything for tracking purposes. The access points and hub are configured to transmit and receive signals (RSSI, link quality, and TOF) between each other. Any motion of a person through the room will change the RF reflection patterns of the radio waves within the room which can be measured by the access points. An algorithm or a classifier such as a neural network, Gaussian mixture model, or k-means classifier may then be used to determine a person's location to specific regions within the room with an accuracy of 2-3 meters. The tag-free mode of operation can also determine whether one or more people are present in a room, which is of critical importance for use in monitoring social interaction.

This innovation represents a significant improvement over the state-of-the-art (IR-based monitoring technologies, which have only room-level present/not-present accuracy) enabling unobtrusive monitoring of movement patterns, walking speed, and measures of overall activity. The tag-free system could be a replacement technology for IR-based monitoring, which typically delivers only binary room-level information localization, or where one needs to be able to identify when multiple people are present.

Innovation 3: Advanced approach to auto-calibration to achieve a simple "plug-and-play" installation.

No matter how beneficial or useful a tag-based or tag-free senior monitoring system may be, no one will ever use it if it is too difficult to install and use. Current tag-based systems that use RSSI as the location metric, for example, can take days of collecting data in every room to carefully calibrate, and then repeated calibration is often necessary every month. This adds significant cost to the maintenance of such systems. This is where the current invention provides a third innovation. The system uses a method called simultaneous localization and mapping (SLAM) for automatic calibration. SLAM will enable the access points to determine their geometric location and necessary calibration parameters within a home automatically by sending wireless messages to each other and assessing their relative position based on TOF measurements. Implementation of SLAM will minimize any calibration that will be required for the system to function properly such that a user of the system will be able to simply plug the access points into their wall sockets at home and begin monitoring.

Innovation 4: Designed to monitor activities of daily living, assess health changes over time, and provide emergency alerts.

The tracking and movement monitoring capability of the system described in this invention will also enable automated extraction of observations or activities of daily living (ADL). The system includes extraction of such metrics as number of trips to the bathroom or time spent in the kitchen, as well as other indicators of activity such as variance in walking speed, or time spent in bed, sitting, or walking. While a few companies (WellAware, GrandCare) offer monitoring of ADL based on IR motion and contact type switches, this invention describes a newer better solution combining both tracking and advance mobility assessment through either tag-based or tag-free modes.

The system will be capable of sending emergency alerts to family members, friends, or health care professionals in the event that something has changed significantly in the older person's health status. If the person has developed a change in activity pattern due to a fall or a stroke, the system will detect that and send an alert so that someone may be dispatched to help the older person. If the older person has slipped and fallen in the shower and they are lying in the bathroom, the system will automatically send an alert message to a family member of what has occurred.

Innovation 5: Information system (IS) to enable seniors to be monitored by friends, family and health providers.

The system described in this invention is designed to be scalable, allowing it to be used to track one person living alone in an apartment or as many as hundreds of people living within an assisted living environment. Each tag will have a unique ID associated with it that will allow the system to independently track multiple people either within a home or an assisted living care facility. One implementation of the system has been designed to work at the 2.4 GHz digital spread-spectrum (DSS) frequency using a custom self-correcting ad-hoc wireless network configuration. A server is described which includes a database and Internet application running on a server for storing movement patterns and for sending alerts to friends, family members, and health care providers in the event of an emergency. In addition to being used in the home health and assisted living settings, it will be useful for research groups using the system to study drugs, surgery and other therapy that impacts mobility and activity; de-identified data of movement patterns can be available to researchers in real time using a standard web browser or mobile computing device such as a phone. This information system (IS) provides a further opportunity for innovation as it leverages the ubiquitous availability of cell phones to enable the creation of a social network of older adults and friends, all living independently within their own homes who can then self-monitor each other using the system.

Patent Reviews: Many patient monitoring devices are designed to capture and record physiologic data and send it to a central software application. For example, US Patent Publication No. 20060235281 "Wireless patient monitoring system" by Mark Joseph Tuccillo (Assignee: Ivy Biomedical Systems, Inc.) uses sensors and a transceiver to capture and send physiologic data like that captured by an ECG monitor or oximeter to a central clinical system as the patient moves through a hospital. U.S. Pat. No. 6,870,484 "Patient monitoring systems having two-way communication" by James Brinsfield and Michael F. Steinike similarly transmits physiologic data to a central clinical system and receives data from the system. US Patent Publication No. 20040102683 "Method and apparatus for remotely monitoring the condition of a patient" by Sukhwant Singh Khanuja et al. remotely monitors physiologic data such as blood pressure, pulse rate, blood glucose, weight, pulse oximetry and others. The invention described herein differs from these patents because it extracts health status information using movement patterns rather than physiologic data.

Other patient monitoring systems monitor for the patient's physical location within an interior environment, but do not use TOF, RSSI and link quality data for continuous monitoring. For example, U.S. Pat. No. 7,666,151 "Devices and methods for passive patient monitoring" by Patrick K. Sullivan et al. uses piezoelectric sensors placed on a flat surface or pad that the patient may frequent such as a chair, wheelchair, or under a layer of bedding, to monitor the patient's location. Numerous inventions are designed to monitor the location of individuals within an interior environment who are not necessarily older or frail; for example, some of these devices detect when an intruder has entered a home or other building. Other inventions are designed to monitor the basic location of inventory items.

US Patent Publication No. 20090322513 "Medical emergency alert system and method" by Franklin Dun-Jen Hwang et al. tracks the location and physiologic data of multiple older adults in an assisted living facility, retirement community or other similar defined community using a wearable device by measuring receiver signal strength indicator (RSSI) or time of flight (TOF) data within a defined interior or exterior environment. The invention also tracks the position of each patient using GPS data, which is useful for capturing location data when the patient leaves the defined interior and exterior environment. The invention sends location and physiologic data to a remote monitoring station in a central monitoring center with trained individuals and some physicians. The wearable device relies on an impact sensor to determine if the person has fallen. It also uses a microphone that captures a high-frequency yell followed by moans from the patient to determine that the patient has fallen.

The current invention is different from the invention described in this patent publication primarily because the current invention uses position and mobility information as the metric for determining if an emergency has occurred—for example if the person's walking speed has changed, it could be an indication that a stroke has occurred. Or if the person is twice as active as they have been over the prior 6 months, perhaps they are suffering from a urinary track infection. Patent Publication no. 20090322513 uses the position information only to notify emergency personnel of the individual's location if an emergency is detected. The position and mobility information is not used to detect or monitor the health status of the individual. In Patent Publication no. 20090322513, the physiologic data that is transmitted by the system is what is used to determine the health status of the individual, not the mobility information. Furthermore, while time-of-flight is mentioned briefly in the description of the patent, the claims only mention RSSI as the metric for determining the position of the individual within the environment. Whereas, the current invention specifically claims use of time-of-flight information, RSSI, and link quality for determining the position of the individual when using tag-free tracking.

Some patient monitoring systems use optical signals to detect motion. U.S. Pat. No. 7,196,317 by Kenith Meissner et al. uses optical signals and the interruption of these signals that occur as a means of detecting motion.

U.S. Pat. No. 7,394,385 "Comprehensive monitoring system" by Thomas S. Franco, Jr. and William G. DiMario discloses an invention that determines if an individual has fallen using a patient-worn accelerometer or plurality of accelerometers. Franco and DiMario use sensors to collect some patient physiologic data and environmental data such as humidity and temperature, and use receiver signal strength indicator (RSSI) measurements to determine patient location. Franco and DiMario do not use time-of-flight information to determine the patient's location. Furthermore, their system does not include a tag-free method of determining the individual's location.

U.S. Pat. No. 6,466,125 "System and method using impulse radio technology to track and monitor people needing healthcare" by James L. Richards et al. uses wideband technology and pulses to enable a patient to notify medical personnel if an emergency has occurred and to help medical personnel determine an emergency victim's location once they arrive on the scene of the emergency. As with patent publication no. 20090322513, this patent does not use movement patterns to monitor health status, but only to identify where the person is located should they indicate themselves that an emergency has occurred by pressing a button. Furthermore, this invention does not describe a tag-free method of monitoring health status should the individual fail to wear their tracking tag, whereas the current invention does include this functionality.

U.S. Pat. No. 6,466,609 "Method for wireless information transfer" by Manfred Koslar et al describes the use of chirp spread-spectrum (CSS) to determine an individual's position, while U.S. Pat. No. 6,404,338 "Measuring and/or security system" by Manfred Koslar discloses using CSS to determine an individual's position for detecting the distance of an object or person and for determining when that object has been moved; for example, in the case of an object, if the object has been stolen. These patents are different from the current invention because they are not using the position information to assess health status or send emergency alerts in the case of a change in health status.

U.S. Pat. No. 6,753,782 "System for monitoring older adults with Alzheimer's disease or related dementia" by Michael W. Power uses RSSI to monitor the behavior, behavior patterns, and movements of older adults with Alzheimer's disease or related dementia as well as other conditions such as autism, attention deficit disorder (ADD), or schizophrenia by placing a detector at the location of a hazard or other location to be monitored and determining when the patient gets too close or far away from the location. Power's invention uses RSSI for tag-based patient localization, while the current invention uses time-of-flight as the metric for tag-base patient localization.

SUMMARY

In one general aspect, the invention relates to a system for monitoring the location, movement and health of one or more individuals within an environment by a monitoring individual. The system used includes one or more optional monitoring devices including a wireless transceiver, a plurality of access point devices including a wireless transceiver, a hub access point device including a wireless transceiver, and a local computing device. The system has the capability of monitoring the location, movement and health of the one or more individuals with or without the monitoring devices being carried or worn upon the body of the individual.

The one or more optional monitoring devices are configured to be carried or worn upon the body of the individual, the wireless transceiver of the monitoring device being configured to measure a time of flight (TOF) value of a radio signal sent between the monitoring device and the at least one wireless transceiver located within at least one access point device. The monitoring device optionally comprises software programmed to use the measure of time of flight value to determine the distance between the monitoring device and the one or more access point devices and transmit a signal representing the distance that has been determined.

The plurality of access point devices are configured to be mounted in at least one room, the wireless transceiver of each access point device being configured to broadcast to and receive radio frequency signals from the one or more optional monitoring devices, other access points within the room and the central hub. The transceivers within the access point devices that measure a time of flight value of a radio signal sent between the one or more optional monitoring devices and the one or more access point devices optionally comprise software to use the measure of time of flight value to determine the distance between the one or more optional monitoring devices and each access point device and transmit a signal representing the distance data. The one or more access points are configured to transmit and receive signals between access points and measure a change in one or more of signal strength, link quality, or TOF of the transmitted signals and transmit a signal representing the measured change in one or more of signal strength, link quality, or TOF. The change in signal strength, link quality or TOF are caused by multipath reflections and absorptions of the radio frequency signal off of the individual being monitored.

The central hub access point device is in communication with the one or more optional monitoring devices, the plurality of access point devices and the local computing device and is configured to transmit data to the local computing device. The central hub access point device is configured to receive the measure of time of flight value or distance from the one or more optional monitoring devices and change in one or more of signal strength, link quality, or TOF from the plurality of access point devices and to transmit the data received.

The local computing device is configured to be operated in the vicinity of the central hub access point device to receive from the central hub access point device the measure of time of flight value and change in one or more of signal strength, link quality, or TOF and is programmed with software configured to aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation.

The system has the capability to operate with or without the measure of time of flight value from the one or more optional monitoring devices such that the system has the capability of monitoring the location, movement and health of an individual whether or not the individual is wearing the monitoring device.

Embodiments of the system may include one or more of the following features. For example, the access point devices and the central hub access point device may be configured to broadcast to and receive radio signals from other access point devices for automatically self-calibrating one or both of the location of the access point devices relative to each other within the room(s), and a parameter used to modify the distance calculation.

The self calibration of the location of the access point devices and/or the parameter used to modify the distance calculation may be one or both of a simultaneous localization and mapping (SLAM) algorithm and dual-Kalman filtering.

The system may further include a remote computing device and a mobile computing device, wherein the local computing device is configured to transmit and the remote computing device is configured to receive data relating to one or more of the individual's 3-d position, velocity, acceleration, mobility, health status, activities of daily living, and determination of the individual experiencing an emergency situation, and wherein the remote computing device may be configured to one or both of transmit health status and emergency alerts to the mobile computing device.

One or both of the remote computing device and the local computing device may be programmed with software using an algorithm that uses the measure of time of flight value to compute one or more of the position, velocity and acceleration of the individual within the facility. The algorithm used to estimate the position, velocity and acceleration of the individual within the environment may be a sigma point Kalman filter, sigma-point Kalman smoother, sigma-point Kalman particle filter, or variant thereof.

The local computing device may include an algorithm to distinguish between activities related to an emergency situation and a non-emergency situation and may be programmed with software that uses the analyzed data from the local computing device to do one or both of: cause alerts to be distributed to mobile computing devices of approved third-party entities when a probable emergency situation has occurred; and analyze and prepare data for use in continuously updated dashboards or reports that display on mobile devices of approved third-party entities. The emergency and non-emergency events may include one or more of falls, changes in gait, changes in average walking speed, changes in rooms visited during a period of time, and changes in activities of daily living including one or more of cooking, sleeping, sitting, eating, socializing, walking, entering or leaving a room, using a computer, going outside, going for a walk, going to the store, using the bathroom, going to a movie, or watching the television.

The local computing device may include software programmed to receive data representing a floor-plan of the rooms and optionally the position of objects within the rooms that represents a digital representation of the rooms and optionally the position of objects within the room. The local computing device may include software to control a procedure to calibrate position measurements with actual locations or way points within a room. The one or more optional monitoring devices may include one or more of a 3-axis accelerometer, a 3-axis gyroscope, a barometric pressure sensor, a digital compass, and a global positioning system sensor for outdoor movement monitoring that are used for one or more of precise movement monitoring, walking speed, posture estimation, gait monitoring, and fall detection.

The system may be configured to operate with the measures of time of flight between one or more optional monitoring devices and one or more access points such that the system monitors and tracks individuals using data from the monitoring devices.

The system may be configured to operate without the measures of time of flight between one or more optional monitoring devices and one or more access access points such that the system monitors and tracks individuals without using data from the monitoring devices. The local computing device may be configured to calibrate the system using data from the monitoring devices at a first time such that the system can be used without the individuals wearing the monitoring devices at a second, later time.

The system may be configured such that movement of the individual within a range of transmission of the one or more access point devices causes changes in one or more of the signal strength, the time of flight (TOF) and the link quality of the radio signals received by the access point devices. The system may be programmed with software to process a change in one or more of signal strength, TOF and link quality to determine the location of an individual within the room based on multipath reflections and absorption of the radio signal as it hits the individual moving through the facility and wherein the signal strength, link, and/or the TOF information measured by the access point devices and broadcast to the central hub access point device are used by the local computing device as inputs to an algorithm to determine the location of the individual within the facility.

The one or more transceivers may use one or both of chirp spread spectrum (CSS) and ultra wideband (UWB) as the method for estimating TOF. The local computing device may be integrated into the central hub access point device. The monitoring device may further include an emergency button or user interface that can be activated to transmit a signal to the local computing device that an emergency has occurred.

In another general aspect there is provided a method for using a system to monitor the location, movement and health of one or more individuals within an environment by a monitoring individual. The system used in the method includes one or more optional monitoring devices including a wireless transceiver, a plurality of access point devices including a wireless transceiver, a hub access point device including a wireless transceiver, and a local computing device, and the system having the capability of monitoring the location, movement and health of the one or more individuals with or without the monitoring devices being carried or worn upon the body of the individual. The method includes the steps of:

using the one or more optional monitoring devices carried or worn upon the body of the individual to measure a time of flight (TOF) value of a radio signal sent between the optional monitoring device and the at least one wireless transceiver located within the plurality of access point devices;

using the plurality of access point devices mounted in at least one room to one or both of measure a time of flight value of a radio signal sent between the one or more optional monitoring devices and access point devices and measure a change in one or more of signal strength, link quality, or TOF of the transmitted signals between access point devices;

receiving at the central hub access point device the measure of time of flight value from the one or more optional monitoring devices and change in one or more of signal strength, link quality, or TOF from the plurality of access point devices and transmitting the data received by the central hub access point device to the local computing device; and using the local computing device to receive from the central hub access point device the optional measure of time of flight value and the change in one or more of signal strength, link quality, or TOF and aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation.

In the method, the system may be used with or without the measure of time of flight value from the one or more optional monitoring devices and whether or not the individual is wearing the monitoring device.

Embodiments of the method may include one or more of the following features or the features described above. For example, the optional one or more monitoring devices may include software programmed to use the measure of time of flight value between the monitoring devices and the access points to determine the distance between the monitoring device and the one or more access point devices and transmit a signal representing the distance that has been determined.

The wireless transceiver of each access point device may be configured to broadcast to and receive radio frequency signals from the one or more optional monitoring devices, other access points within the room and the central hub access point device, and wherein the transceivers within the access point devices that measure a time of flight value of a radio signal sent between the one or more optional monitoring devices and the one or more access point devices optionally comprise software to use the measure of time of flight value to determine the distance between the one or more optional monitoring devices and each access point device and transmit a signal representing the distance data and wherein the plurality of access points are configured to transmit and receive signals between access points and measure a change in one or more of signal strength, link quality, or TOF of the transmitted signals and transmit a signal representing the measured change in one or more of signal strength, link quality, or TOF, whereby the change in one or more of signal strength, link quality or TOF is caused by multipath reflections and absorptions of the radio frequency signal off of the individual being monitored.

The central hub access point device may be configured to receive the measure of time of flight value from the one or more optional monitoring devices and change in one or more of signal strength, link quality, or TOF from the plurality of access point devices and to transmit the data received.

The local computing device may be configured to be operated in the vicinity of the central hub access point device to receive from the central hub access point device the measure of time of flight value and change in one or more of signal strength, link quality, or TOF and is programmed with software configured to aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation.

In another general aspect there is provided system for monitoring the location, movement and health of one or more individuals within an environment by a monitoring individual, the system including a plurality of access point devices including a wireless transceiver, a hub access point device including a wireless transceiver, and a local computing device.

The plurality of access point devices are configured to be mounted in at least one room, the wireless transceiver of each access point device being configured to broadcast to and receive radio frequency signals from the other access points within the room and the central hub access point device. The transceivers within the access point devices are configured to transmit and receive signals between access point devices and measure a change in one or more of signal strength, link quality, or TOF of the transmitted signals and transmit a signal representing the measured change in one or more of signal strength, link quality, or TOF. The change in signal strength, link quality or TOF are caused by multipath reflections and absorptions of the radio frequency signal off of the individual being monitored.

The central hub access point device is in communication with the plurality of access point devices and the local computing device and is configured to transmit data to the local computing device. The central hub access point device is configured to receive the measure of change in one or more of signal strength, link quality, or TOF from the plurality of access point devices and to transmit the data received.

The local computing device is configured to be operated in the vicinity of the central hub access point device to receive from the central hub access point device the measure of change in one or more of signal strength, link quality, or TOF and is programmed with software configured to aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation.

Embodiments of the system may include one or more of the following features. For example, the system may include one or more of the features described above or discussed herein.

In another general aspect there is provided a system for monitoring the location, movement and health of one or more individuals within an environment by a monitoring individual. The system includes one or more monitoring devices including a wireless transceiver, a plurality of access point devices including a wireless transceiver, a hub access point device including a wireless transceiver, and a local computing device.

The one or more monitoring devices are configured to be carried or worn upon the body of the individual, the wireless transceiver of the monitoring device being configured to measure a time of flight value of a radio signal sent between the monitoring device and the at least one wireless transceiver located within at least one access point device. The monitoring device optionally comprises software programmed to use the measure of time of flight value to determine the distance between the monitoring device and the one or more access point devices and transmit a signal representing the distance that has been determined.

The one or more access point devices are configured to be mounted in at least one room, the wireless transceiver of each access point device being configured to broadcast to and receive radio frequency signals from the one or more monitoring devices, other access points within the room and the central hub. The transceivers within the access point devices that measure a time of flight value of a radio signal sent between the one or more monitoring devices and the one or more access point devices optionally comprise software to use the measure of time of flight value to determine the distance between the one or more monitoring devices and each access point device and transmit a signal representing the distance data.

The central hub access point device is in communication with the one or more monitoring devices, the one or more access point devices and the local computing device and is configured to transmit data to the local computing device. The central hub access point device is configured to receive the measure of time of flight value from the one or more monitoring devices and to transmit the data received.

The local computing device is configured to be operated in the vicinity of the central hub access point device to receive from the central hub access point device the measure of time of flight value and is programmed with software configured to aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation.

In the system, the software of the local computing device is programmed with one or more of a sigma point Kalman filter algorithm, sigma-point Kalman smoother, sigma-point Kalman particle filter, or variant thereof that uses the measure of time of flight value measured between the monitoring device and the access points to compute one or both of the position, velocity and acceleration of the individual within the facility.

DETAILED DESCRIPTION

The inventors have developed a position tracking and mobility assessment system to address the problems described above that uses two methods to remotely assess an older person's health using mobility and position information. The system consists of two methods of mobility estimation: 1) a tag-based mode of operation which requires the older adult being monitored to wear a tag on their wrist, ankle, or around their belt or otherwise on their clothing or body, and 2) an unobtrusive passive tag-free position estimation mode of operation which requires no compliance by the older adult being monitored for the case where the older person forgets or chooses not to wear the tag.

One important aspect of the tag-based tracking is the use of a sigma-point Kalman Filter (SPKF). While the SPKF has been used by the inventors in a number of tracking related applications, for example using RSSI based methods and ultrasound-based methods, in this invention, the inventors specifically reformulated the Rauch-Tung-Striebel sigma point Kalman smoother (RTSSL-SPKS), which works as a fixed-lag smoother, in order to accommodate Time-of-flight (TOF) range data from multiple access points. The estimated state consisted of the 2-D position, walking speed, and orientation of the person being tracked. The inventors have formulated and simulated a SLAM framework in the tracking system, which corresponds to simultaneously estimating the state of the person (position and velocity) and the parameters of the TOF based sensor observation model. Parameters correspond to the 2D locations along with the scales and offsets of each transceiver to account for multi-path and other measurement errors. This is implemented using a dual technique in which two filters are run simultaneously: one SPKS to track the person given the current estimated parameters, and a second SPKF to estimate the parameters given the current estimated location of the person. Additional details on the tag-based algorithm development have been presented by the inventors.

Figure 10:
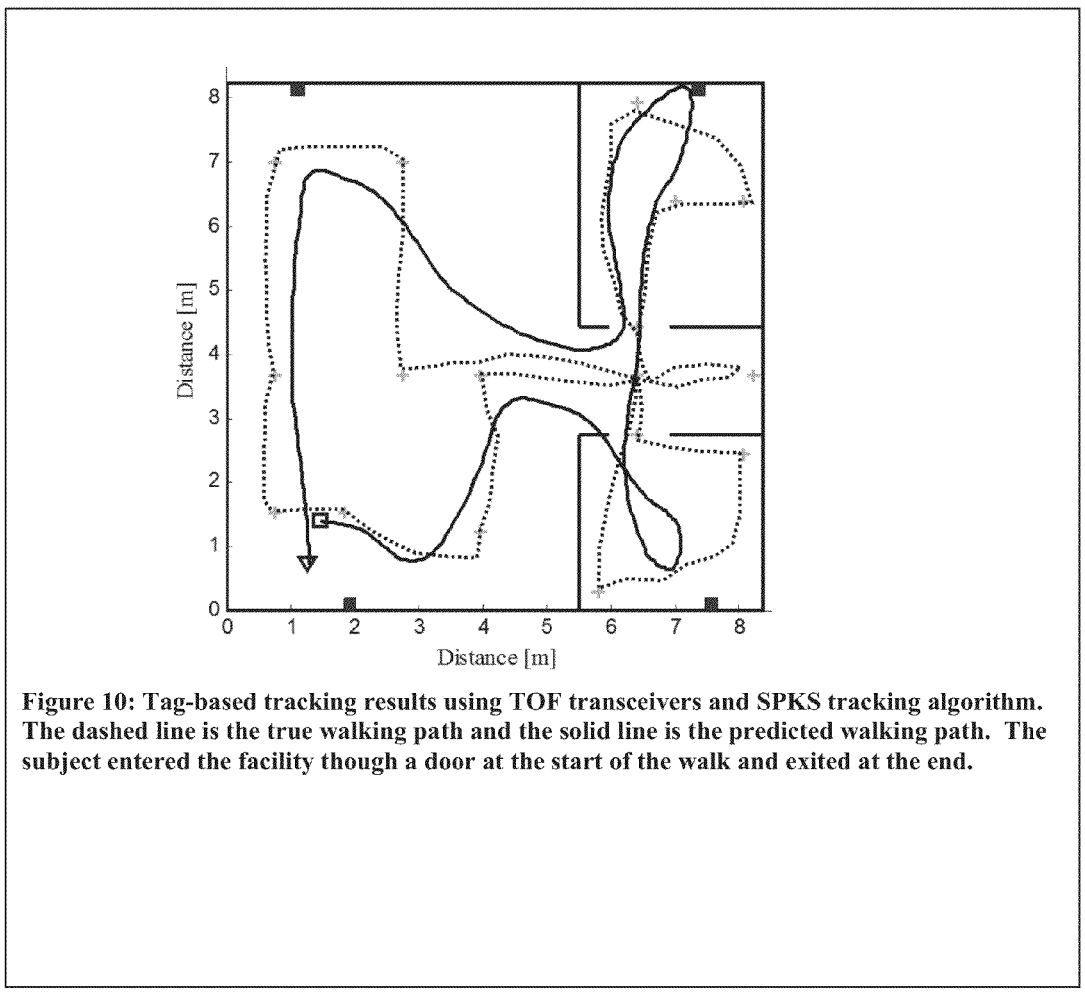
FIG. 10 is a graph showing the predicted and actual walking path according to the invention using TOF transceivers and a SPKS tracking algorithm.

To demonstrate performance and reduce the invention to practice, a test subject carried a tag containing a nanoLOC (Nanotron Ltd) transceiver that periodically (12 Hz) transmitted and received information from each of the access points mounted around the room. The tag relayed the TOF information acquired from each of the access points to a hub connected to a laptop. Tracking estimates were performed offline using the SPKS. The space used for testing was a small multi-room facility, approximately 8 m×8 m in size, consisting of one main room and two side rooms, and was cluttered with boxes and furniture as is common in a typical living space. In the study, 3 subjects were consented and asked to walk several pre-determined paths at varying speeds passing through specific waypoints. Subjects returned on 3 separate occasions to repeat the experiments. FIG. 10 illustrates the performance of the SPKS based tracking solution when a subject was asked to follow a specific waypoint path. Approximate root-mean-square-error (RMSE) for the SPKS relative to the known waypoints was 0.55 m, compared to 0.9 m for an EKF based solution and 1-2 m accuracy for the Nanotron supplied tracking software.

The results illustrated in FIG. 10 were achieved using a simple manual calibration scheme. The invention includes an aspect relating to the steps and process by which calibration can be automated using SLAM. The inventors have completed the implementation of SLAM and tested using a simulation. However, the development tags using the Nanotron transceivers are currently only providing TOF measurements between the tag and access points, but not between access points to access point. This reduces the number of total available observations from $M^2$ to just M, where M is the number of access points, which is insufficient for convergence of the algorithms. The results are sufficient for the purpose of tracking but the resulting accuracy is further improved when there also is TOF measurements between the tag and AP as well as between AP and AP. With all of the TOF between AP to AP, the autocalibration using SLAM is improved and eliminates the need for manual calibration, thereby further improving the results.

Further, the tag-based tracking system described in this invention can be used to monitor the location and mobility of older adults in a multi-patient or multi-resident facility, such as an assisted living facility, if the older adults being monitored wear a tag transceiver. Each tag would include a unique patient ID in the data packets it sent to the access points so that the data from individual older adults could be analyzed and viewed separately from that of other monitored older adults. The invention can be used to monitor individuals in non-patient-based situations, such as when a parent asks a relative or friend to monitor them. As should be understood, in some embodiments the invention can be used to monitor any individual whose health should be monitored and the monitoring can be based on movement of the individual. As such, the invention is not limited to elderly and older patients.

The tag includes an emergency button that the patient or some other individual may press to send an automatic alert to a monitoring individual or to automatically dial 911 or in some other way contact a health provider to obtain immediate emergency medical services for the patient.

The tag could optionally include a digital GPS unit to track the patient's location when the patient is not within the interior environment. The invention could also include an altimeter to measure the distance relative to sea level to help determine what floor the person is on in a multi-storied patient care facility.

Figure 11:
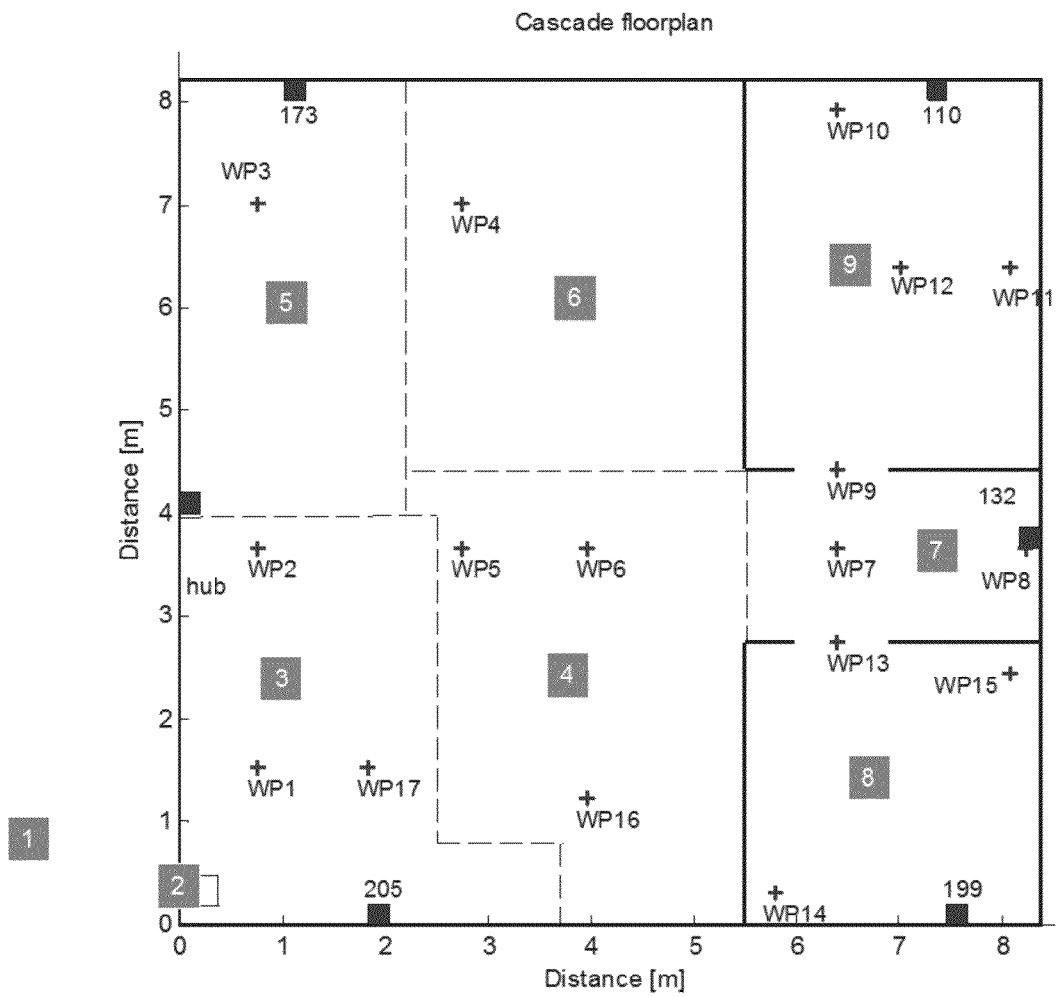
FIG. 11 is a plan view show the placement of access points in a room for a tag-free tracking system.

Even when the person being monitored forgets or refuses to wear their tag, the invention described herein can still monitor their mobility at 2-3 meter accuracy using the tag-free tracking mode. The same wall-mounted access points and hub used in the tag-based tracking mode are used in tag-free mode; however, no tag or time-of-flight ranging is required. Receiver signal strength indicator (RSSI) is measured from access-point to access-point and from access-point to hub. FIG. 11 shows how the room was separated into 9 different regions for a tag-free tracking experiment. The shaded numbers indicate how the rooms were divided into regions with region 1 being outside the room and region 2 being the opening of the door.

The invention used in the experiment includes a classifier which was designed to estimate the person's location within the room using both the mean and variance of the RSSI recorded over a sliding window of time. Three types of classifiers were tested to determine optimal performance: 1) Gaussian mixture models (GMM), 2) multi-layer perceptron neural network (MLP-NN), and 3) k-nearest neighbor (KNN). Data collected to train the classifiers consisted of RSSI recording corresponding to a person walking randomly for 90 seconds in each known region. The recordings from two different subjects were used for training.

Figure 12:
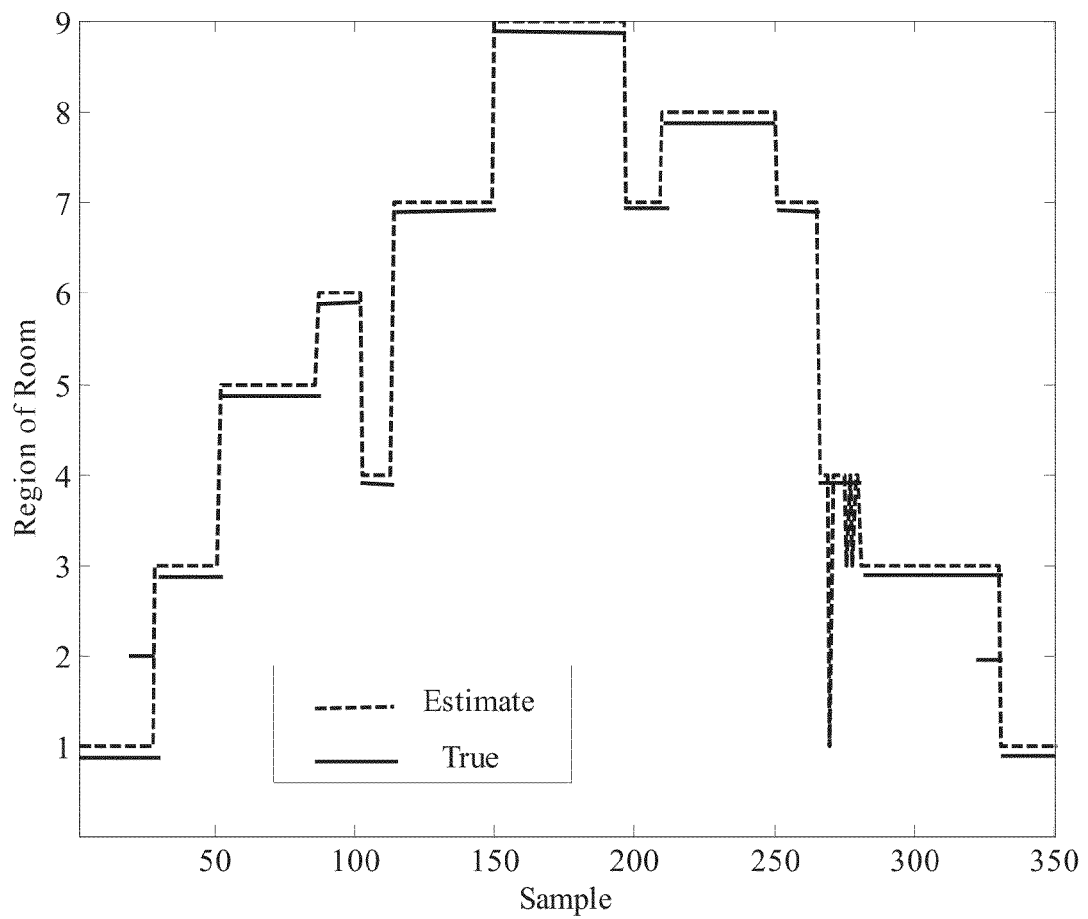
FIG. 12 is a graph showing the estimated and actual movement in a tag free environment.

Experiments consisted of having a person walk a path with and without carrying a tag. When a person carried a tag, the tag-based tracking was performed simultaneously with the tag-free tracking for verification purposes. When no tag was worn, only the tag-free solution was activated. As with the tag-free experiments, 3 subjects were consented and asked to walk multiple routes at varying speeds on multiple visits. One subject at a time was present in the facility during tracking. In a representative trial, a person started outside of the room and then walked along the WP1 to WP9 path shown in FIG. 11 and then exited the room. FIG. 12 shows the performance of the NN based classifier. Overall, the tracking classification was remarkably accurate considering no tag was carried. The classification was not as accurate only during some transitions between regions of the room, but mostly the classification accurately displays the walking path of the person in the room. Results comparing the three tag-free classification methods (GMM, NN, and KNN) indicated that all three are good choices for classifying position, with the NN showing slightly better performance. Overall, region based classification was better than 95% with an approximate equivalent location accuracy between 2-3 meters. An additional study was performed to determine whether it was possible to discriminate between 1 or 2 person occupancy. Based on these results, we have demonstrated the feasibility to perform tag-free tracking and have successfully achieved accuracy of 2-3 meters without the use of a tag.

Figure 1:
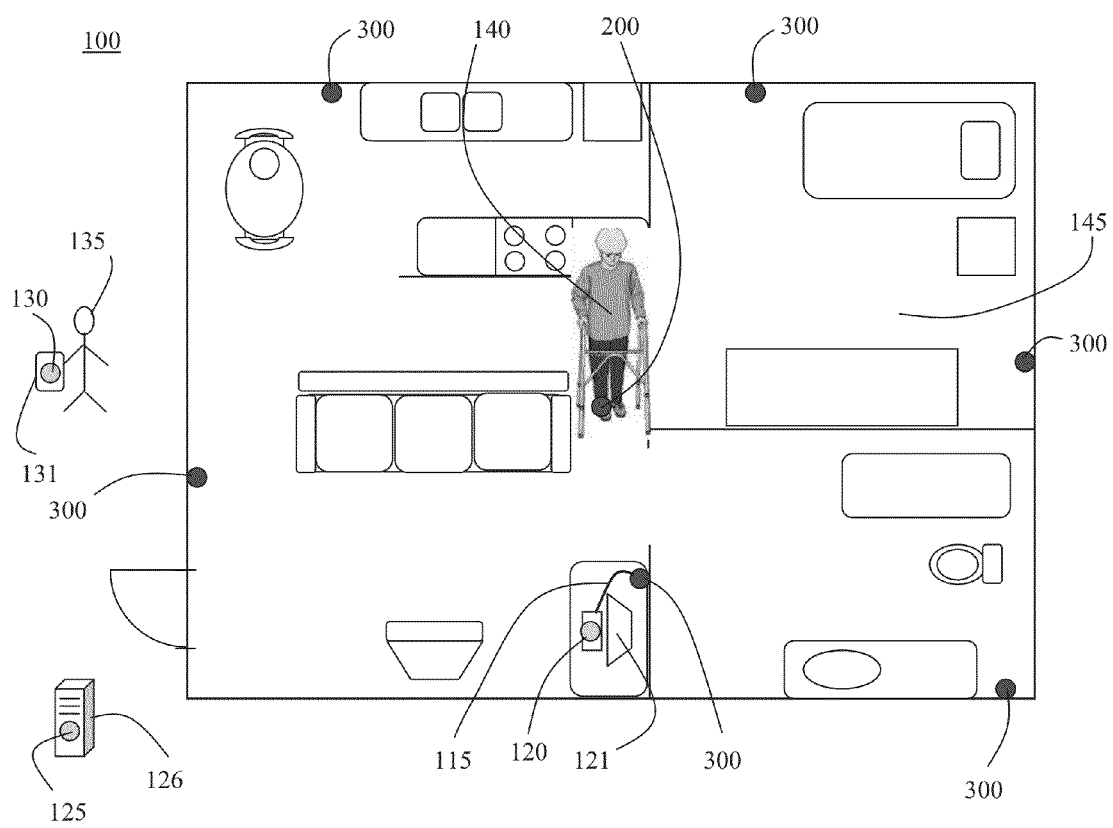
FIG. 1 is a plan view of a position tracking and mobility assessment system with a tag in use. (TAG PLAN)

The inventors have developed a Position Tracking and Mobility Assessment System as shown by the drawings in FIGS. 1 through 12. FIG. 1 provides a plan view of the overall Position Tracking and Mobility Assessment System 100 in use with a patient 140 in an interior environment 145, including the individual components of the system. These components include a patient-worn tag 200 that is further illustrated in FIG. 2 and FIG. 4a; multiple access points 300, further illustrated in FIG. 3 and FIG. 4b; a local version of the position tracking and mobility assessment software 120 running on a local computing device 121; version remote computing device component of the position tracking and mobility assessment software 125 running on a remote computing device 126; and a mobile computing device component of the position tracking and mobility assessment software 130 running on a mobile device 131 that belongs to a third party entity 135. One of the access points 300 connects to the local computing device 121 using a USB connection 115.

Figure 2:
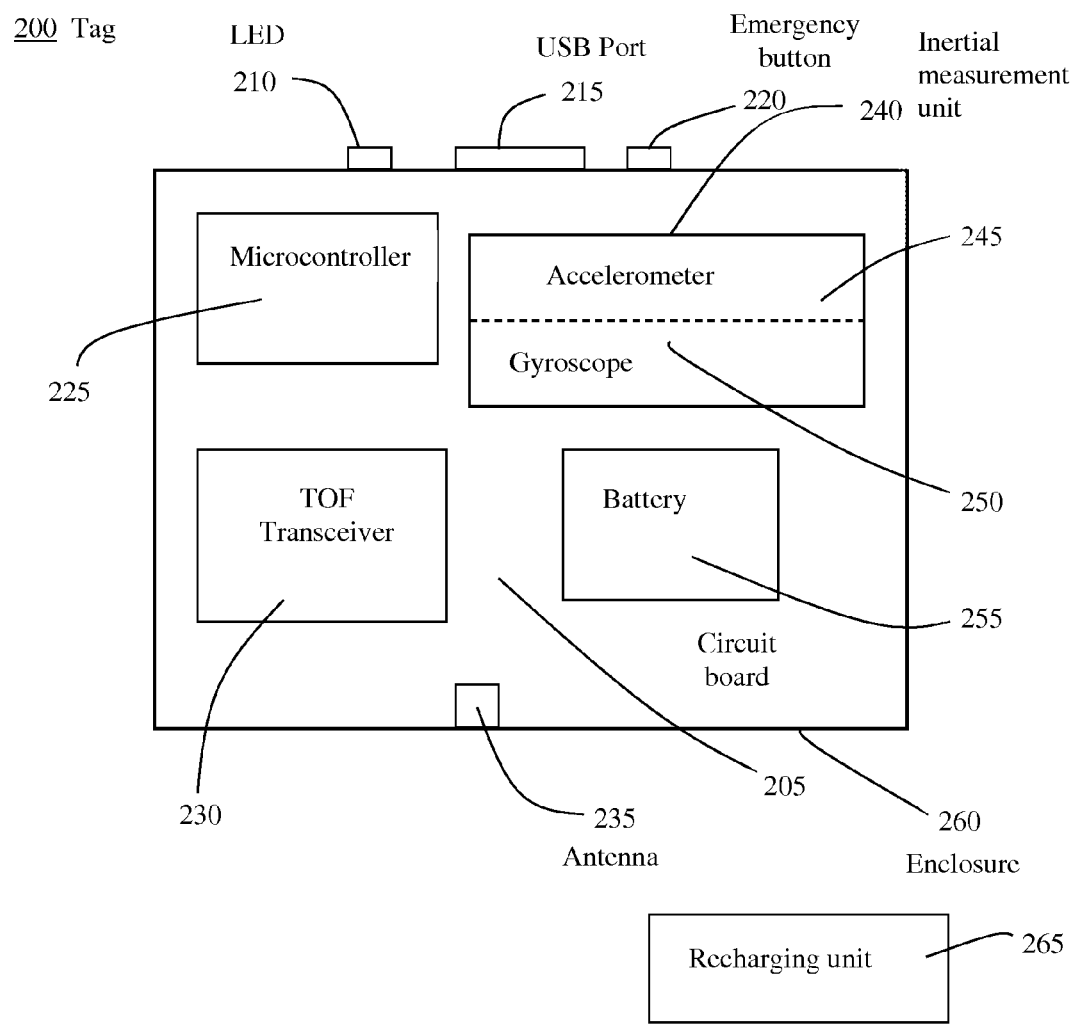
FIG. 2 is a representative diagram of a tag.

FIG. 2 illustrates the tag 200. The tag 200 comprises a circuit board 205 to which is attached an LED light 210, a USB port 215, an emergency button 220, a microcontroller 225, a time of flight (TOF) transceiver 230, an antenna 235, an inertial measurement unit (IMU) 240, and a battery 255. The IMU 240 includes the following two items: a digital 3-axis accelerometer 245 and a digital 3-axis gyroscope 250. An enclosure 260 surrounds the contents of the tag 200.

Numerous TOF transceivers are commercially available for use today. For example, a digital spread-spectrum wireless transceiver such as the NanoLOC transceiver available from Nanotron Technologies could be used in the tag. Similarly, numerous IMUs are commercially available that could be used in the tag. One such IMU is the IMU-3000 available from Invensense, Incorporated, with a built-in 3-dimensional gyroscope and a bus that can connect to a 3-axis accelerometer. One such accelerometer that is commercially available is the ADXL346 from Analog Devices. The tag could use a separate 3-dimensional gyroscope and a separate 3-dimensional accelerometer, or may combine both on a single IMU. Numerous microcontrollers are also commercially available that could be used in the tag. One such microcontroller is the PIC18LF2645 from Microchip Incorporated.

The size of the tag 200 will be similar to that of a wristwatch. The design of the enclosure 260 will either include a strap or include the ability to add a strap such that the patient 140 can wear it around his or her wrist, ankle, or other location on the body. A separate recharging unit 265 enables the battery 255 in the tag to be recharged. The emergency button 220 is positioned in such a way that the patient 140 can easily press the button to trigger an alert to the mobile device 131 of a third-party entity 135 monitoring them. Pressing the button would also automatically call 911 to provide information to an emergency services individual that would be sufficient to help them send out emergency medical aid to the patient 140.

In a different embodiment of the tag 200, the tag 200 may also include one or more of the following components: a digital unit to measure barometric or atmospheric pressure, a digital GPS unit, and a 3-axis digital compass. The atmospheric pressure unit could be used to help determine patient location in the case where the patient 140 lives in an environment with multiple levels; for example, if the patient 140 lived in a three-story house or in an assisted living facility with multiple floors connected by stairs and elevators. The GPS unit could be used to track the patient's location when the patient exits the interior living environment 145. The 3-axis digital compass could be used to determine patient orientation such as the direction the patient 140 is facing.

A major benefit of the tag 200 is that it includes various power-mode settings that allow the patient to trade off tracking accuracy with battery life. These settings allow the system to capture location tracking and mobility assessment data less frequently based on the discretion of the patient or care provider. It also allows for the capture of only some of the possible data sources. For example, by capturing only TOF and accelerometer 3-dimensional acceleration data, the unit can operate for up to four weeks without needing to be recharged. In general, the tag TOF transceiver 230 requires little power to operate, but by reducing the frequency of data capture or the number of data sources captured, the unit can run much longer before needing to be recharged.

Figure 3:
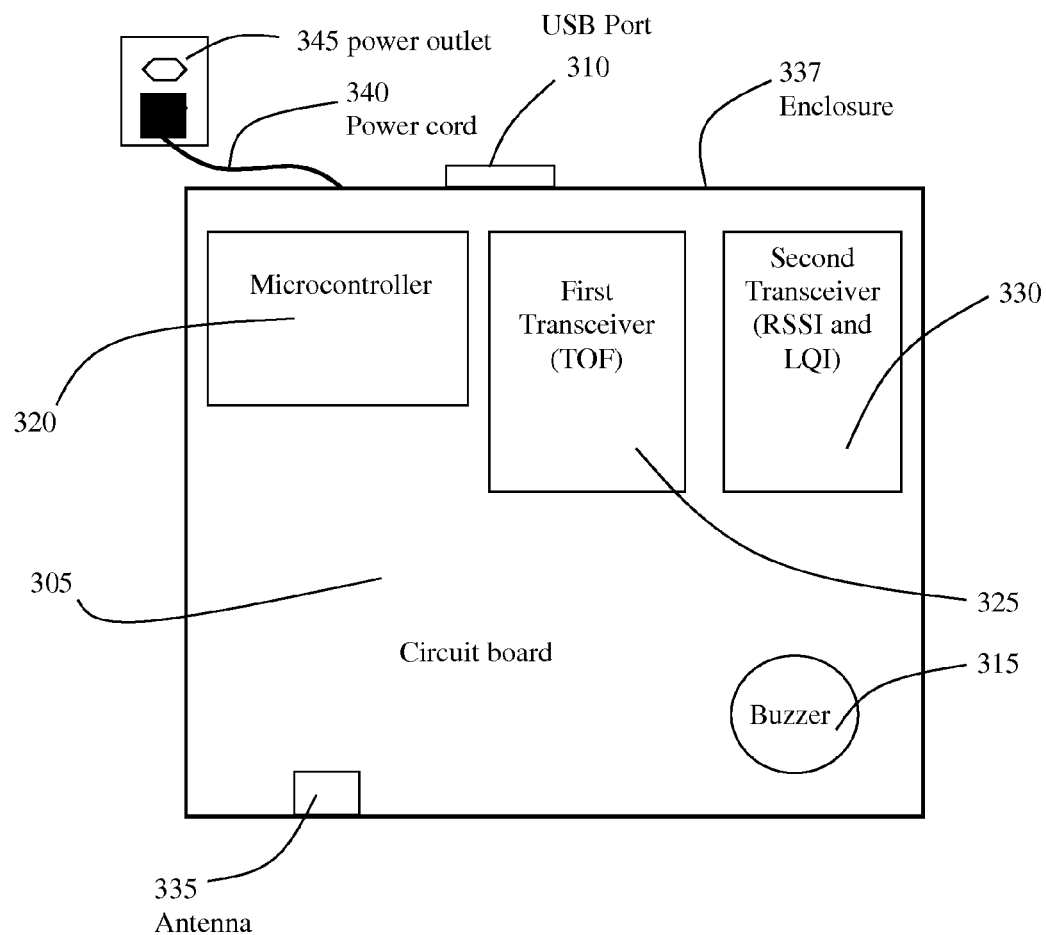
FIG. 3 is a representative diagram of an access point.

FIG. 3 describes one of the multiple access points 300. Each access point 300 comprises a circuit board 305, to which is attached a USB port 310, a buzzer 315, a microcontroller 320, a transceiver that can measure TOF and return signal strength indicator (RSSI) 325, optionally a second transceiver that only measures RSSI and link quality indicator (LQI) 330, and an antenna 335. An enclosure 337 surrounds the contents of each access point 300. Each access point 300 includes an electrical power supply cord 340 that extends from the enclosure 337 and plugs into an electrical wall outlet 345 to provide power to the access point 300.

Each access point 300 could use the NanoLOC transceiver from Nanotron or some other commercially available TOF transceiver. Similarly, each access point 300 could use a commercially available microcontroller such as the PIC18LF2645 microcontroller from Microchip Incorporated. Each access point could use one of many commercially available RSSI/LQI transceivers. One such RSSI/LQI transceiver is the CC1101 transceiver from Texas Instruments.

As mentioned earlier, the position tracking and mobility assessment system includes three versions of custom software. FIG. 1 shows that the local computing device version of the software 120 is installed on the local computing device 121. The local computing device could be a desktop computer, a laptop, a pad device, or some other computing device capable of running the software. This local computing device version 120 may include a database to aggregate and store positional and mobility data. The software version 120 also includes algorithms that process the data to determine patient location, along with activities of daily living (ADLs) such as cooking, sleeping, sitting, eating, socializing, walking, entering or leaving a room, using a computer, going outside, going for a walk, going to the store, using the bathroom, going to a movie, or watching the television. The software version 120 also includes algorithms that process the data to determine probable emergency events such as "Patient Suffered Fall," and "Patient Not Moving." Primarily, the software version 120 relies on two algorithms to analyze the data for patient location and mobility: one algorithm is for tag-based position tracking and mobility assessment and the other is for tag-free position tracking and mobility assessment. One algorithm that may be used to determine patient position using the TOF data and other mobility data collected by the tag is the sigma-point Kalman filter (SPKF) state-space estimation algorithm.

This local computing device version of the software 120 can be configured with a variety of settings; for example, the local computing device version of the software can be used to import the floor plan of the house such that important household rooms and items are indicated by relative position such as the kitchen, bedroom, bathroom, living room, table, chairs etc. This software 120 can also be used to run a calibration routine that can be used to improve the accuracy of identifying the household rooms and items within the house.

The remote computing device version of the software 125 is installed on a remote computing device 126. This version of the software 125 is used to register third party entities 135 who will monitor the patient 140. As such, all versions of the software will ensure HIPAA compliance and compliance with other patient data privacy regulations, to the extent necessary. This version of the software 125 is also used to automatically review ADLs and probable emergency events, and when necessary, to distribute alerts to third party entities 135 monitoring the patient 140. The remote computing device version of the software 125 is also used to transmit general health status data to the mobile device 131 of each third party entity 135 monitoring the patient 140 so that these entities 135 can monitor the status of the patient 140 in real time through reports, dashboards, and other means of communicating health status.

The mobile device version of the software 130 is installed on the mobile device 131 of a third party entity 135. Such a mobile device 131 might be a smart phone, a pad computer, a laptop, or some other mobile device that can run the mobile device version of the software 130. This version of the software 130 may be configured so that the third party entity 135 can receive specific types of alerts such as a text message, a noise such as an alarm going off, an email or a call with a recorded message. The mobile device version of the software 130 can also include a set of graphs or incorporate color to provide near real-time health status updates through a dashboard or other graphical user interface element that provides an immediate view of the patient's status. For example, the words "Patient Fallen" might be written in red to indicate an emergency situation. In contrast, "Patient Sleeping" may be written in green. A patient's gait may be shown in a graph that indicates speed over time. If the patient's speed is slowing over time, such as might occur when a patient is suffering a physical ailment of some type, the graph might change from green to yellow, and then to red. These dashboard views would be available continuously, and alerts of emergency events could be received at the same time, overriding the dashboard updates. For example, an emergency event could pop up a text message that displays on top of a health status dashboard.

Although the present invention has been described as comprising a monitoring device, access points, a hub, a server, and a mobile computing device, it is possible that a smaller subset of these components may be used in a different configuration to monitor the health of an individual. For example, if the invention is being used to monitor multiple older adults in an assisted living facility, the system may be designed to only consist of the monitoring device(s), access points, and hub. Perhaps the assisted living facility does not wish to send the patient health information to a server or a mobile computing device. Instead, the general health status information is only displayed at the local computing device that is connected to the hub for use by the assisted living facility staff.

In another design of the system, the server may not be used, but instead the computing device connected to the hub sends the health status information directly to the mobile computing device. In this alternative design, the local computing device may collect the raw data, process it with the algorithms, and distribute alerts and health status by email, text message, an automated call, or some other standard communications means to mobile devices that would be running the mobile device version of the software. This design of the system would not require a server and could be designed as a simpler version of the invention in which individuals or close friends or family members wish to monitor an individual without the requirement of having the patient's health status information being stored on a remote server.

In another embodiment of the invention, the mobile device does not necessarily need to have a mobile version of the software 130 installed. The remote computing device version of the software 125 may be able to alert a third party entity using a more simplified means. For example, the software 125 could send an automated text message, call with an automated message, or send a pager alert to notify the third party entity that the patient may potentially have suffered a medical emergency.

When using the invention to monitor a single patient, as shown in FIG. 1, the position tracking and mobility assessment system 100 is set up such that the patient being monitored 140 wears the tag 200 on his or her ankle, wrist or other location on the 140 body or clothing. Multiple access points 300 are plugged into electrical outlets throughout the interior environment 145 in which the patient 140 is being monitored. Alternatively, power could be made available in locations as needed and the access points 300 could be directly wired to the power source. One of the access points 300 is attached to the local computing device 121 by a USB cord 115 or other electronic connecting means, however in another rendition of the design, this access point can be integrated onto the same circuit board and within the same package as the local computing device. As explained in more detail below, the access point 300 connected to the local computing device 121 receives information from the other access points 300 and feeds that to the computing device 121. The access points 300 are located throughout the interior environment 145 such that at all times the tag 200 worn by the patient 140 is within range of the radio frequency signal being broadcast from at least three access points 300. This range is generally between 30 feet and 50 feet. The access points 300 should also be located such that each access point 300 can transmit and receive a radio frequency signal with at least two other access points 300. Similarly, this range is generally between 30 feet and 50 feet.

The patient 140, a family member, a friend, healthcare provider, or some other capable individual installs the local computing device version of the position tracking and mobility assessment software 120 on the local computing device 121 in the interior environment 145 in which the patient 140 is being monitored. Similarly, a capable individual installs the remote computing device version of the position tracking and mobility assessment software 125 on the remote computing device 126. Further, the one or more third-party entities 135 who are monitoring the patient 140, or some other capable individual, installs the mobile device version of the position tracking and mobility assessment software 130 on the mobile device 131 of each third party entity 135. A capable individual configures the mobile device version of the software 130 so that the individual receives specific alerts and specifies the means by which he or she wishes to receive those alerts.

When the patient 140 is wearing the tag 200, and the battery 255 in the tag 200 has power, the TOF transceiver 230 in the tag 200 will broadcast a radio frequency (RF) signal at a periodic interval. The transceiver within the tag uses a low-power wireless communication technology such as chirp spread spectrum (CSS) and broadcasts the signal periodically such as every 250 ms to each of the access points within the environment. The access points 300 will receive the signal from the tag 200. The access points 300 will then send a signal back to the tag 200 providing the round-trip travel time necessary to calculate TOF measurements between the tag 200 and each of the access points. The round-trip TOF data between the tag and each of the access points is then sent to the hub access point. The hub sends this TOF data to the local computing device. The TOF between the tag 200 and each access point 300 can be multiplied by the speed of light (i.e., $3.0 \times 10^8$ meters/second) to calculate the distance between the tag and each of the access points. These distances can be used within a tracking algorithm such as a sigma point Kalman filter tracking algorithm to estimate the location of the tag within the room. In the data packet that the tag 200 sends to the hub access point 300, the tag 200 includes 3-dimensional velocity data and 3-dimensional angle/tilt data provided by the accelerometer 245 and gyroscope 250, respectively, on the tag 200. The accelerometer 245 provides information about the patient's 140 acceleration in any direction. For example, if the patient had fallen, the accelerometer 245 would show an increase in acceleration downward over a short period of time. The gyroscope 250 provides data that indicates the patient's 140 3-dimensional angle of rotation including pitch, roll, and yaw. For example, if the patient had fallen, the gyroscope 250 would show that the patient had tilted from roughly upright (0 degrees) to roughly horizontal (90 degrees) in a very short period of time. The tag 200 would also send additional information in the data packet that could be useful. Once such type of information would be battery power level of the tag 200.

Figure 4A:
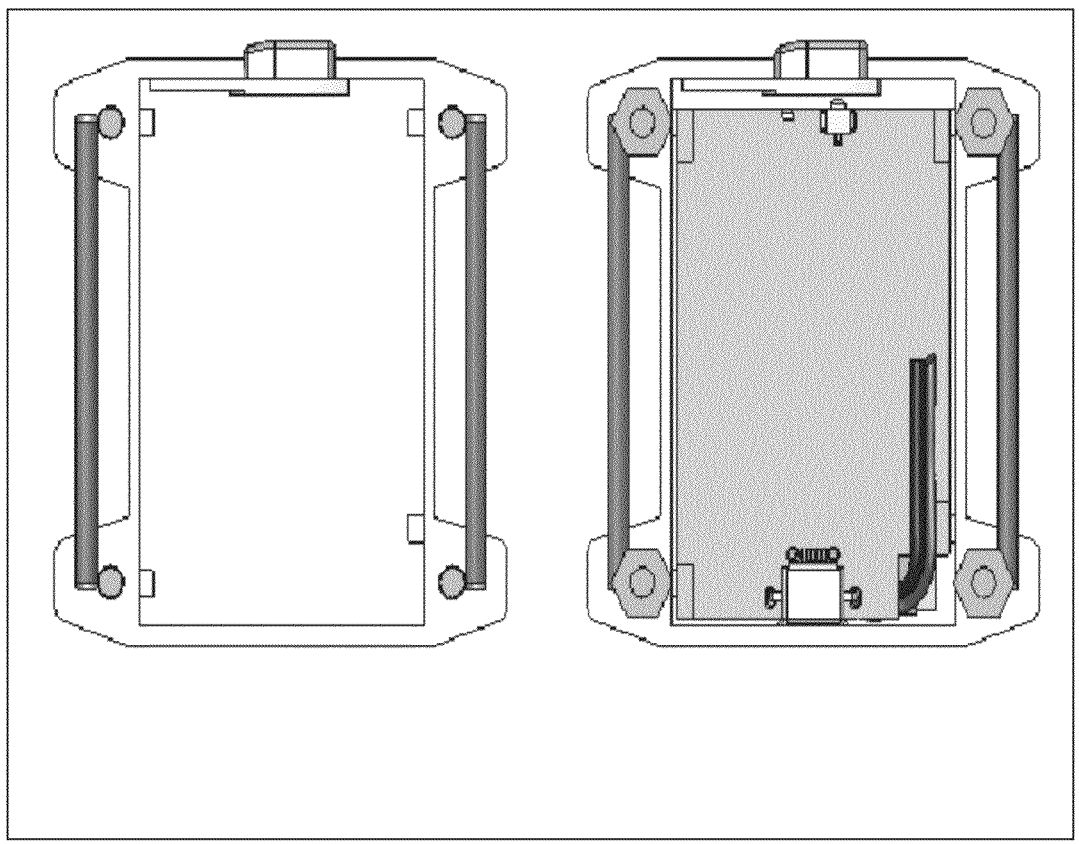
FIGS. 4A and 4B are illustrations of the tag and access point hardware and enclosure prototypes.
Figure 4B:
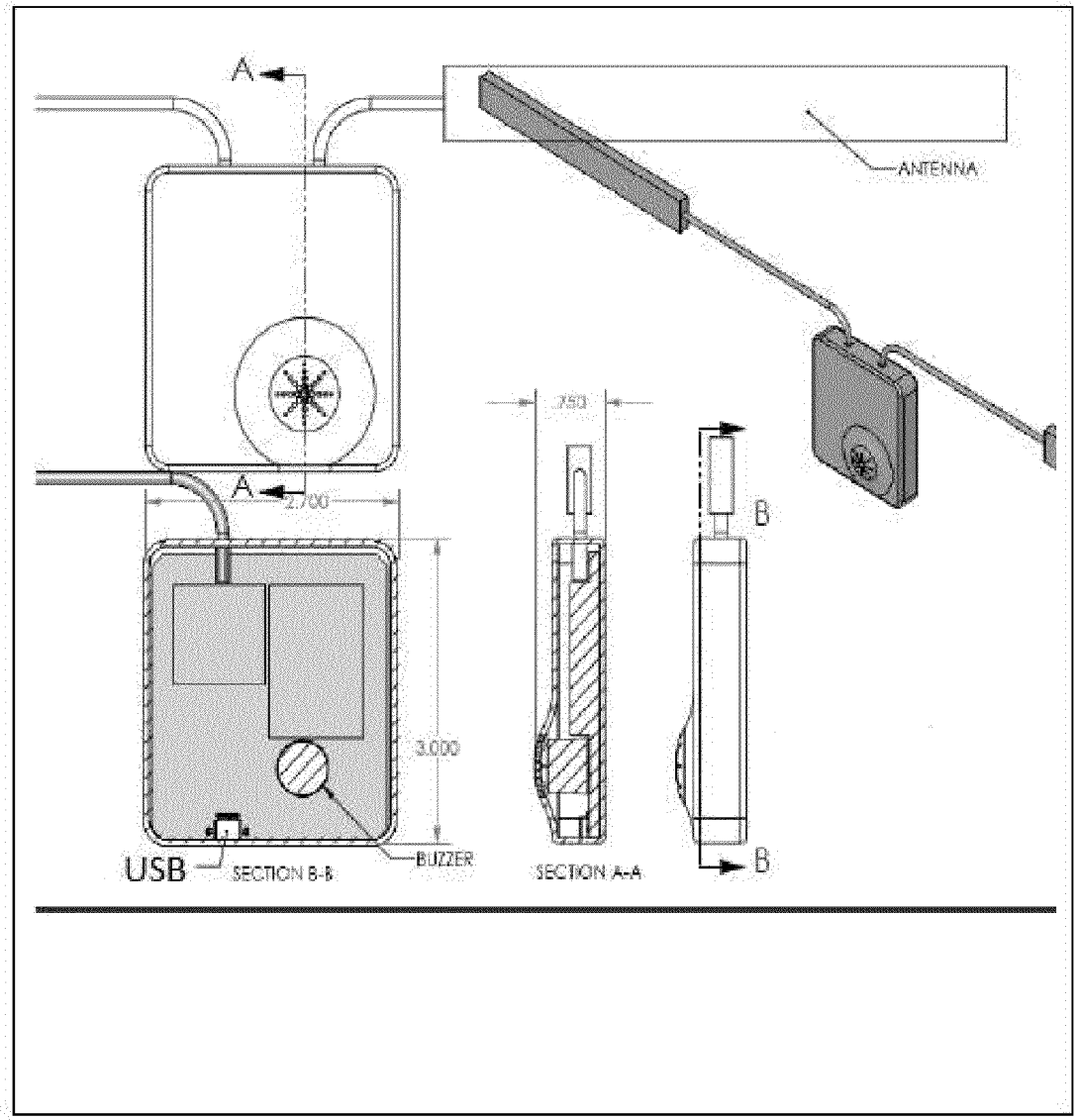

FIGS. 4A-B illustrate a prototype of the tag and access point hardware and enclosures. The tag of FIG. 4A is a tag that can be worn on the wrist, on the ankle, or around the belt or elsewhere on the body or clothing. The dimensions of one embodiment of the tag may have dimensions of 2.25"×1.87"× 0.56" (H W D). The access point hardware of FIG. 4B may be in the form of access points mounted on wall used for both tag-based and tag-free monitoring. The dimensions of one embodiment of the access point hardware may have dimensions of 2.75"×3.0"×0.75" (H W D).

Figure 5:
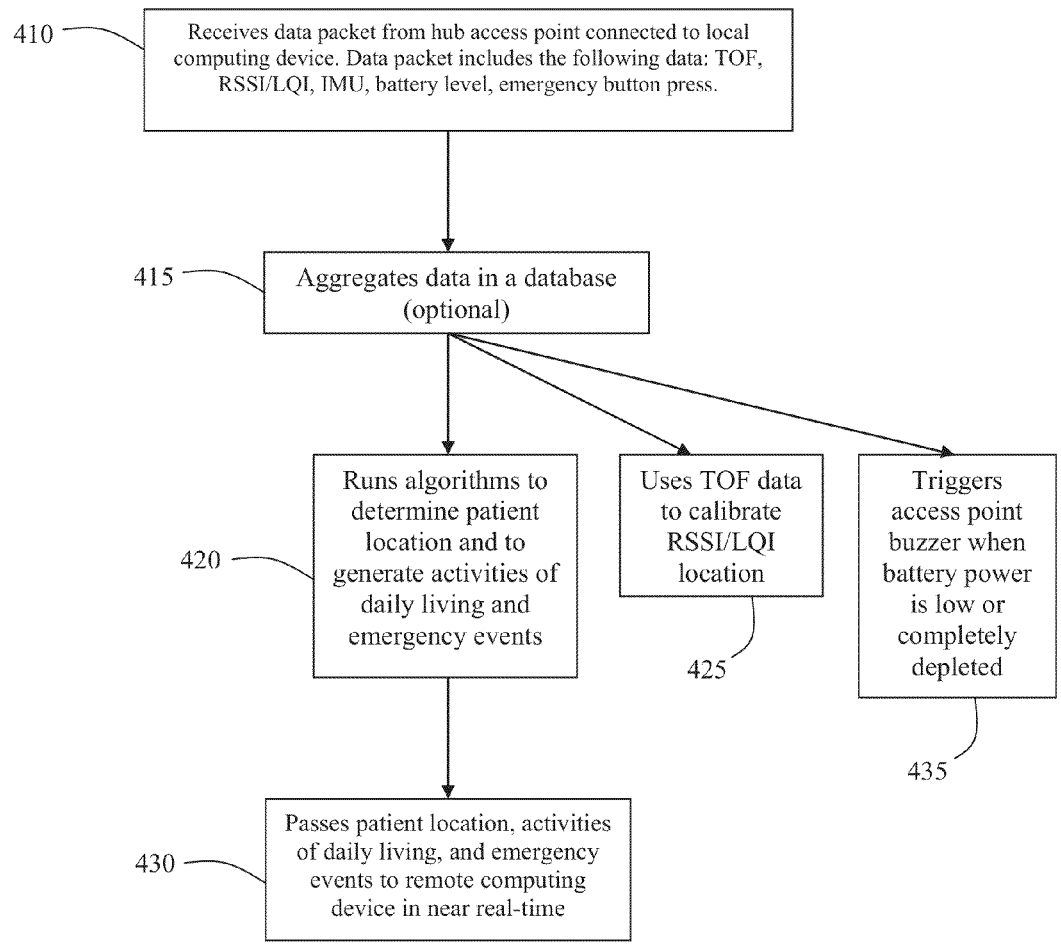
FIG. 5 is a flow chart of the local computing device version of the position tracking and mobility assessment system software.
Figure 6:
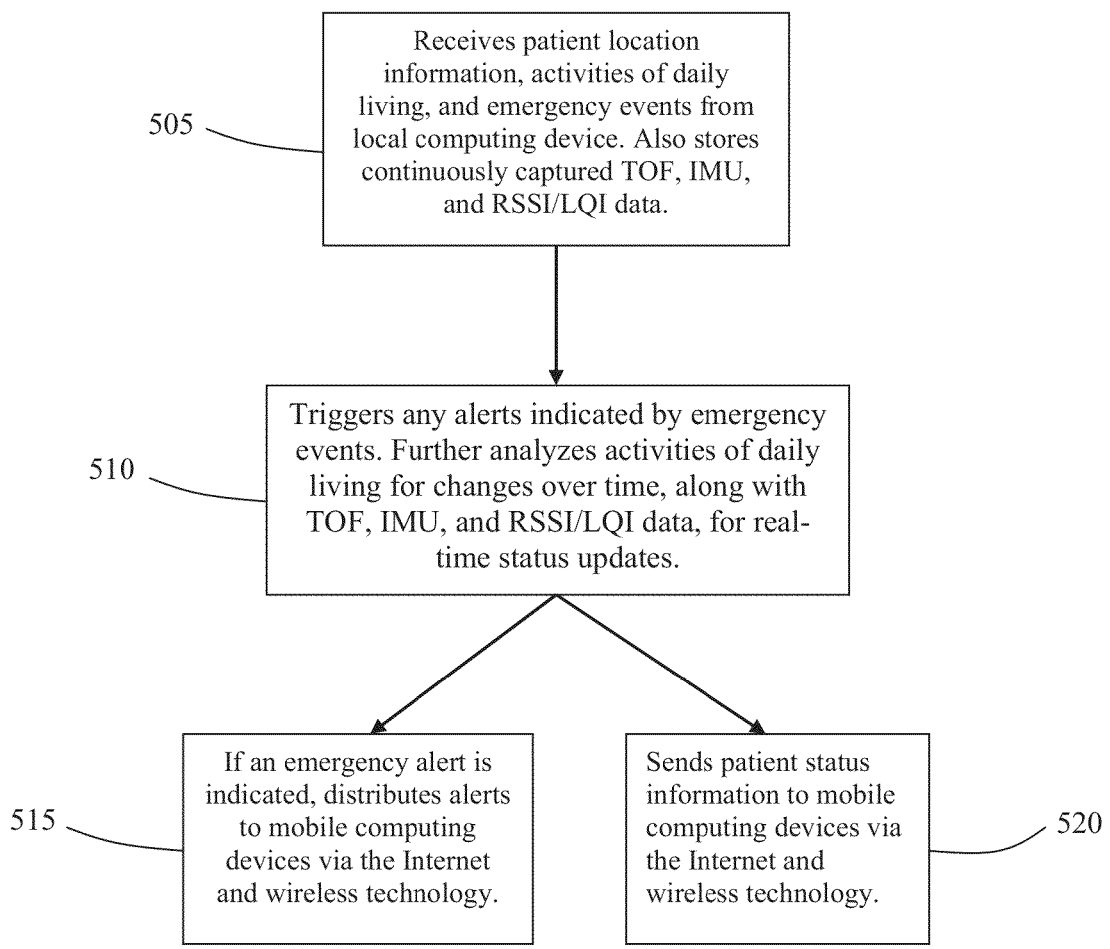
FIG. 6 is a flow chart of the remote computing device used within the position tracking and mobility assessment system software.
Figure 7:
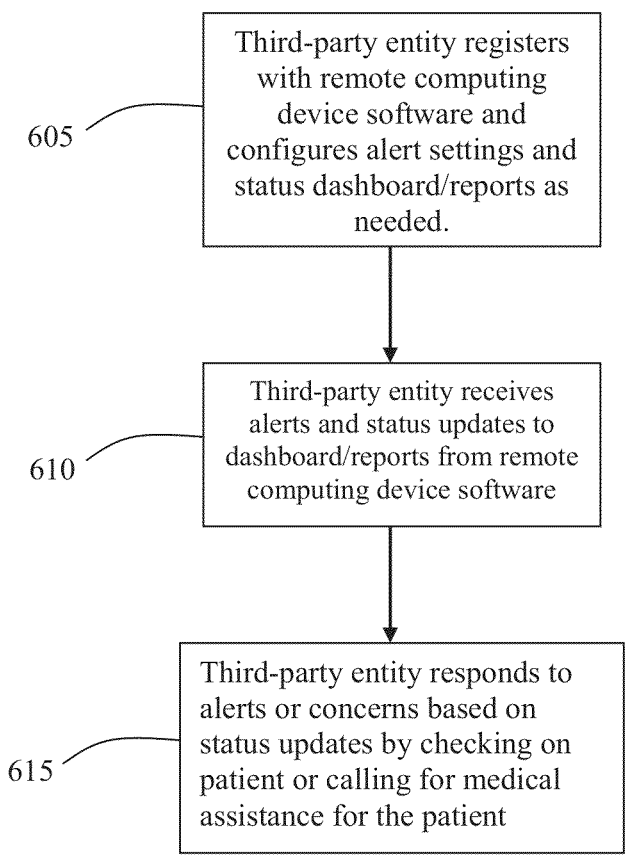
FIG. 7 is a flow chart of the mobile computing device used within the position tracking and mobility assessment system software.

FIGS. 5 through 7 are flow charts that include steps that indicate how the position tracking and mobility assessment system uses the data once it has reached the software version 120 on the local computing device 121.

FIG. 5 illustrates the steps that occur with the data in the local computing device version of the software 120 on the local computing device 121. The software 120 receives the data packet containing the measurements for TOF, RSSI/LQI, IMU (3-dimensional velocity and 3-dimensional angle/tilt), emergency button press, and battery charge level data (step 410). The software 120 optionally aggregates the data in a database such as MySQL or some other commercially available database application (step 415). The software 120 next does several tasks using this data: (1) the software runs the algorithms that calculate the location of the individual using tag-generated TOF measurements between the tag and each of the access points, (2) the software runs the algorithms that calculate the location of the individual using the access point-to-access point TOF, RSSI and LQI measurements, (3) the software runs the algorithm that uses the TOF, RSSI, LQI, and IMU measurements to generate activities of daily living and probable emergency events (step 420); (4) the software uses the TOF data to automatically calibrate and perform minor corrections on the RSSI/LQI location data (step 425); and (5) if the charge for the battery in the tag is low or completely depleted, the software can optionally trigger an indicator message to the patient such as the buzzer 315 on the access points 300 to make a noise that alerts the patient 140 (step 435) that he or she needs to recharge the tag 200 battery 255. The local computing device version of the software 120 then transmits the results of the algorithms in near real-time to the remote computing device 126 (step 430).

FIG. 6 illustrates the steps that occur when the activities of daily living and probable emergencies generated from the algorithm on the local computing device version of the software 120 are sent via the Internet from the local computing device 121 to the remote computing device 126 running the remote computing device version of the software 125. In step 505, the software 125 on the remote computing device 126 receives the patient location data, along with activities of daily living and probable emergencies from the local computing device 121. The software also stores the continuously captured TOF, IMU and RSSI/LQI data for use with populating health status updates.

In step 510, the software 125 reviews the data it receives from the local computing device, including activities of daily living and probable emergencies. If the data includes a probable emergency event, the software 125 triggers an alert. If the software 125 triggers an alert, the software automatically distributes the alert to any mobile devices 131 configured to receive the alerts using the Internet and wireless technology (step 515). As illustrated by step 520, the software 125 also uses the data to provide health status information for dashboards or reports that the third-party entity 135 can see on their mobile device 131. For example, a dashboard on the mobile device version of the software 130 could show a map of the person's movement, the level of patient activity based on the amount of movement over time, characteristics of the patient's gait, how often the person has been in the kitchen to prepare meals, or how long the patient spends sitting down eating meals.

The software is not limited to these examples of position tracking and health status information, and can be programmed to provide much more status information based on the need of the patient and the desire of the caregiver or person monitoring the patient for specific types of information. In addition, this information can be updated in near-real time. Alternatively, rather than seeing continuous updates on a mobile device 131, the entity 135 monitoring the patient 140 could set the time period for automatic updates to health status information dashboards or reports, or might choose to update the health status information by clicking a button in the mobile device user interface of the invention software. In such cases where real-time updates were not desired, the third party entity 135 would still be alerted if the patient 140 experienced an emergency event.

In addition to the steps shown in FIG. 6, the remote computing device version of the software 125 may be programmed to required third party entities to register to be given access to the patient's position and mobility status data and to receive alerts on their mobile device. This registration process in the software 125 ensures that only approved entities may view the patient's personally identifiable health information to ensure compliance with applicable local, state and federal patient health data privacy laws (for example, HIPAA).

FIG. 7 illustrates the steps that occur when the remote computing device version of the software 125 sends an alert or health status information to the mobile device version of the software 130 installed on the mobile device 131 of a third party 135 entity who is monitoring the patient 140. The mobile device 131 could be a smart phone such as the iPhone or an Android phone; a mobile computing device such as a laptop or a pad computer; or some similarly mobile computing device with a user interface on which an application may be installed.

In step 605, the third-party entity 135 monitoring the patient 140 registers with the remote computing device software and configures the alert settings and health status update dashboards and specifies the reports to receive. Once they have registered and are an approved user, the third party entity 135 receives alerts and status updates distributed by the remote computing device software (step 610). If the third-party entity 135 receives an alert that the patient 140 has suffered a medical emergency or they are concerned for the patient's 140 well-being based on health status information, the third-party entity 135 can respond by checking on the patient or by contacting medical personnel for immediate medical assistance for the patient 140 (step 615).

Figure 8:
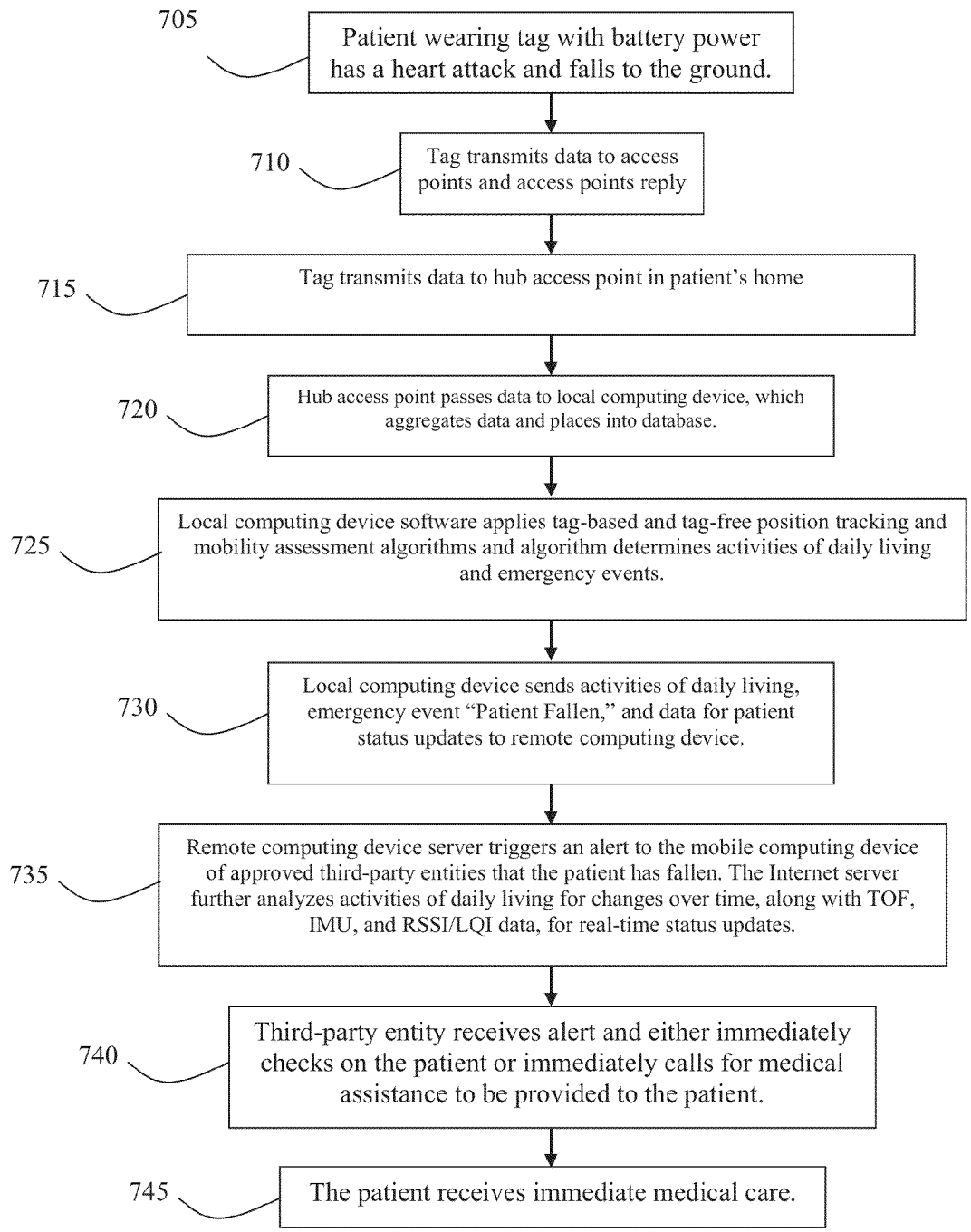
FIG. 8 is a flow chart illustrating a usage scenario of the position tracking and mobility assessment system with the tag in use.

FIG. 8 provides an example of the position tracking and mobility assessment system in use. In step 705, a patient who is wearing a tag with battery power falls. The tag has been receiving TOF data from nearby access points and transmits TOF data, along with IMU data back to any in-range access points (step 710). The access points all relay any data they have received, which includes any data received from the tag, back to the access point connected to a computer in the patient's home (step 715). The access point transmits the data via a USB connection to the local computing device, which aggregates the data in a database (step 720). The position tracking and mobility assessment software on the local computing device applies the tag-based algorithm to determine the patient's location, activities of daily living, and emergency events (step 725). The local computing device sends this information, which now includes an emergency event, "Patient Fallen," along with general health status information, to the remote computing device. The system software on the remote computing device triggers an alert to the mobile device of each approved third-party entity that notes that the patient has fallen. The software further analyzes the activities of daily living and the TOF, IMU, and RSSI/LQI data for changes over time and for real-time patient health status updates (step 730). Each third-party entity receives the alert on their mobile device and either immediately checks on the patient or calls for medical assistance to be provided to the patient by calling 911 or some other health care provider (step 740). The patient then receives immediate medical care (step 745), if needed.

Figure 9:
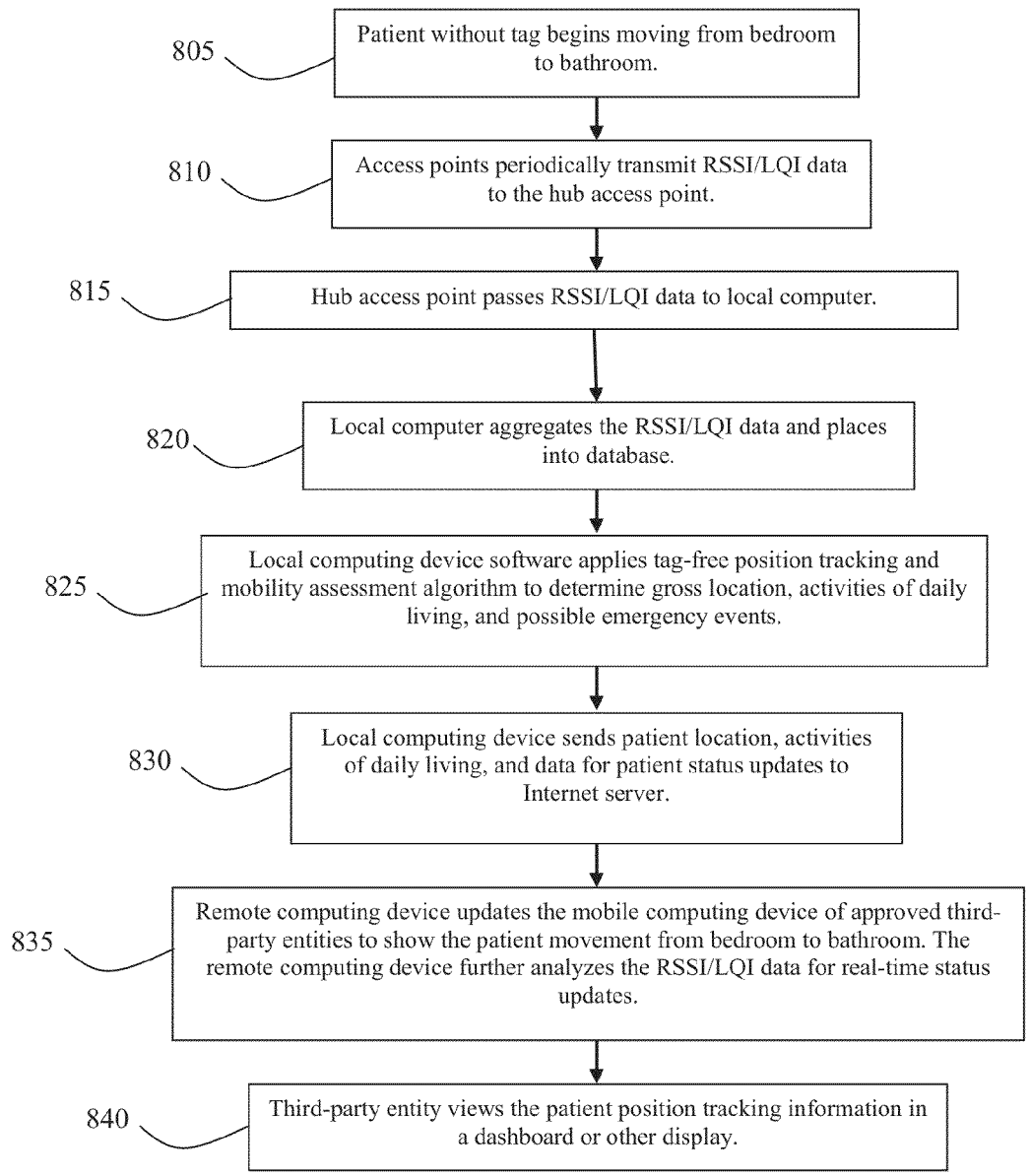
FIG. 9 is a flow chart illustrating a usage scenario of the position tracking and mobility assessment system for a patient without the tag in use.

FIG. 9 provides an example of the position tracking and mobility assessment system in use without the tag transceiver to determine position location. In step 805, a patient who is not wearing a tag begins walking from the bedroom to the bathroom. The access points periodically transmit RSSI/LQI data to the hub access point (step 810). The hub access point then passes the RSSI/LQI data to the local computer (step 815). The local computer aggregates the RSSI/LQI data and places it in a database (step 820). The local computer applies the tag-free position tracking and mobility assessment algorithm to determine the gross location, activities of daily living, and any possible emergency events (step 825). The local computer sends the patient location, activities of daily living, and data for patient status updates to the remote computing device (step 830). The remote computing device updates the mobile device of approved third-party entities to show the patient movement from the bedroom to the bathroom and the server software further analyzes the RSSI/LQI data to supply information for real-time status updates (step 835). Any of the approved third-party entities can view the patient position tracking information in a dashboard or other display to see the patient's movement from the bedroom to the bathroom (step 840).

In another embodiment of the invention, the position tracking and mobility assessment system may be used to monitor multiple older adults in a multi-patient facility, such as an assisted living facility or a graduated care facility. In these cases, each patient monitoring would wear a tag, and each tag would include a unique patient ID that could be used to track the individuals.

In the case of an assisted living facility, the local computing device could be in a nurses' station or other similar central location within the interior environment in which multiple individuals are being monitored. The Internet server could be the same computing device as the local computing device or it could be a separate computer.

If the individuals being monitored live in separate residences, each individual would require a local computer to receive the position tracking and mobility data, aggregate the data, and send the data to the remote computing device in a main caregiver's facility.

In both cases, alerts could be sent to caregivers by sending a page, sending an email, calling a phone, texting or sending an SMS, or in some other way contacting the caregiver. The alerts could be received by a mobile device application on a mobile device or might be as simple as a text message to a mobile phone or phone call to a landline phone.

In a separate embodiment of the invention, the tag may include a GPS unit to track patient location when they are not within the interior environment with the access points. Such a method would rely on the common mechanism of GPS location tracking that relies on satellites to determine a person's location.

In a separate embodiment of the invention, the tag may include an altimeter to collect data that measures the person's height relative to sea level. This data could be useful for tracking patient's in a multi-storied interior environment such as an assisted living facility that has multiple floors or a multi-storied patient home.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Accordingly, it is not intended that the invention be limited, except as by the appended claims.

The following Appendix provides an explanation of the Sigma Point Kalman Smoother algorithm. As explained above, an important aspect of the tag-based tracking described herein is the use of a sigma-point Kalman Filter (SPKF). As explained above, the algorithm is used in the system to estimate the position and velocity of the individual. While the SPKF has been used by the inventors in a number of tracking related applications, for example using RSSI based methods and ultrasound-based methods, in this invention, the inventors specifically reformulated the Rauch-Tung-Striebel sigma point Kalman smoother (RTSSL-SPKS). This smoother works as a fixed-lag smoother to accommodate Time-of-flight (TOF) range data from multiple access points. The explanation below describes this algorithm in more detail. Additional details and explanation for the algorithm, method of using the algorithm, systems incorporating the algorithm, and applications of the algorithms are provided in the following recent publications, which are incorporated herein in their entirety by reference for their disclosure of tracking systems and their operation and uses, including the algorithms, equipment and applications:

1. E. A. Wan, A. S. Paul, and P. G. Jacobs, "Tag-free RSSI indoor localization," to appear in Institute of Navigation (ION) Technical Meeting, Newport Beach, Calif., Jan. 30-Feb. 1, 2012.
2. A. S. Paul, E. A. Wan and P. G. Jacobs, "Sigma-point Kalman smoothing for indoor tracking and auto-calibration using time-of-flight ranging," In proceedings of The 24th International Technical Meeting of The Institute of Navigation (ION GNSS 2011), Portland, Oreg., Sep. 20-23, 2011.
3. P. G. Jacobs, A. S. Paul and E. A. Wan, "EmbedRF Position Tracking and Mobility Assessment System: A low-power and low-cost system for indoor pedestrian tracking and mobility assessment," In proceedings of The 24th International Technical Meeting of The Institute of Navigation (ION GNSS 2011), Portland, Oreg., Sep. 20-23, 2011.

APPENDIX

Sigma-Point Kalman Smoother (SPKS)

This appendix provides a concise formulation of the SPKS along with the gating used for tracking. While a number of different formulations of the SPKS exist, a fixed-lag SPKS (FL-SPKS) obtains smoothed state estimates using a forward and backward pass within a sliding window. The forward pass uses a standard SPKF that operates on the nonlinear dynamics within a windowed set of L measurements between time $k=j-L$, and $k=j$ to generate the estimate $\hat{x}_k$. A backward smoothing pass, which makes use of the Rauch-Tung-Striebel (RTS) equations (derived using a weighted statistical linear regression formulation of the SPKF), applies a corrective measure on the forward estimation results to generate the smoothed estimates $\hat{x}_k^s$, where the superscript "s" indicates smoothed estimate. The window is then moved forward by one time-step and the same steps described above are repeated between time $k=j-L+1$ and $k=j+1$ to obtain a new $\hat{x}_k^s$. The pseudo-code for the smoother is given below:

Forward filter initialization:

$$\hat{x}_0 = E[x_0], \; P_{x_0} = E[(x_0 - \hat{x}_0)(x_0 - \hat{x}_0)^T]$$

$$\hat{x}_0^a = E[x_0^a] = [\hat{x}_0^T \; \hat{p}_0^T \; \hat{n}_0^T]^T$$

$$P_{x_0}^a = E[(x_0^a - \hat{x}_0^a)(x_0^a - \hat{x}_0^a)^T] = \begin{bmatrix} P_{x_0} & 0 & 0 \\ 0 & Q_0 & 0 \\ 0 & 0 & R_0 \end{bmatrix}$$

while $j \leq N$
1. Forward Filter Recursions:
for $k=j-L, j-L+1, \ldots j$
a) Calculate Sigma Points:

$$\chi_k^a = \begin{bmatrix} \hat{x}_k^a & \hat{x}_k^a + \Lambda & \hat{x}_k^a - \Lambda \end{bmatrix} \text{ where } \Lambda = \sqrt{(\tilde{M} + \lambda)P_{x_k}^a}$$

b) Time-Update Equations:

$$\chi_{i,k+1|k}^x = f_k(\chi_{i,k}^x, \chi_{i,k}^p) \; i = 0, 1 \ldots, 2\tilde{M}$$

$$\hat{x}_{k+1}^- = \sum_{i=0}^{2\tilde{M}} w_i^m \chi_{i,k+1|k}^x$$

$$P_{x_{k+1}}^- = \sum_{i=0}^{2\tilde{M}} \sum_{j=0}^{2\tilde{M}} w_{ij}^c (\chi_{i,k+1|k}^x - \hat{x}_{k+1}^-)(\chi_{j,k+1|k}^x - \hat{x}_{k+1}^-)^T$$

c) Weighted Statistical Linearization of f(.):

$$P_{x_k, x_{k+1}} = \sum_{i=0}^{2\tilde{M}} \sum_{j=0}^{2\tilde{M}} w_{ij}^c (\chi_{j,k}^x - \hat{x}_k)(\chi_{i,k+1|k}^x - \hat{x}_{k+1}^-)^T$$

$$A_{f,k} = P_{x_k, x_{k+1}}^T P_{x_k}^{-1}$$

$$b_{f,k} = \hat{x}_{k+1}^- - A_{f,k} \hat{x}_k$$

$$P_{\varepsilon_{f,k}} = P_{x_{k+1}}^- - A_{f,k} P_{x_k} A_{f,k}^T$$

d) Measurement-Update Equations:

e) Weighted Statistical Linearization of h(.).

$$A_{h,k} = P_{x_{k+1} z_{k+1}}^T (P_{x_{k+1}}^-)^{-1}$$

$$b_{h,k} = \hat{z}_{k+1}^- - A_{h,k} \hat{x}_{k+1}^-$$

$P_{\epsilon_h,k} = P_{Z_{k+1}} - A_{h,k} P_{x_{k+1}}^- A_{h,k}^T.$

End for

2. Backward Smoothing:

for k=j, j−1, j−2, ..., j−L+1, j+L a) Error Covariance Smoothing:

$D_k = P_{x_k} A_{f,k}^T (P_{x_{k+1}}^-)^{-1}$ $P_{x_k}^s = P_{x_k} - D_k (P_{x_{k+1}}^- - P_{x_{k+1}}^s) D_k^t$ b) State Estimate Smoothing:

$\hat{x}_k^s = \hat{x}_k + D_k(\hat{x}_{k+1}^s - \hat{x}_{k+1}^-)$

End for

Increment j by one: j=j+1

End while where:

Parameters: λ is the composite scaling parameter $\lambda = \alpha^2(\tilde{M} + \kappa) - \tilde{M},$ $w_i^c$ and $w_i^m$ are the scalar sigma-point weights defined as:

where M is the dimension of each state, $\tilde{M}$ is the dimension of each augmented state, $Q_k$ is the process noise covariance and $R_k$ is the observation noise covariance. The length of the observation sequence is N and L is the lag between the current measurement and the estimated state. The final smoothed state and state estimation error covariance are denoted as $\hat{x}_k^s$ and $P_{x_k}^s$ respectively. The values of the SPKF parameters used: α=0.85, β=2 and κ=0. Note that these SPKS equations are for a generic nonlinear set of state-space equations, and are applicable for either state or parameter estimation in a dual formulation.

Adaptive Gating:

Adaptive threshold based gating is used in order to eliminate severe multipath TOF measurements. If the absolute difference between an observed TOF range and the predicted range by the SPKS is higher than a threshold, the corresponding TOF observation is eliminated from the set $z_k$. The value of the threshold is adapted depending upon the number of TOF measurements accepted at each time instant. Since three independent tag-transceiver TOF measurements are sufficient for localization, the threshold value is lowered if more than three observations are gated by the SPKS. If gating reduced the number of accepted observations to less than three, the threshold is increased. The SPKS incorporating the adaptive gating technique improves the tracking performance compared to the SPKS without gating.

What is claimed is:

1. A system for monitoring the location, movement and health of one or more individuals within an environment by a monitoring individual, the system comprising a plurality of access point devices in which each access point device includes at least one wireless transceiver, a central hub access point device including a wireless transceiver, a local computing device, and one or more optional monitoring devices including a wireless transceiver, the system having the capability of monitoring the location, movement and health of the one or more individuals with or without the monitoring devices being carried or worn upon the body of the individual, wherein:

the one or more optional monitoring devices are configured to be carried or worn upon the body of the individual, the wireless transceiver of the monitoring device being configured to measure a time of flight (TOF) value of a radio signal sent between the monitoring device and the at least one wireless transceiver located within at least one access point device, wherein the one or more optional monitoring devices comprise software programmed to use the measure of time of flight value to determine the distance between the monitoring device and the one or more access point devices and transmit a signal representing the distance that has been determined;

the plurality of access point devices being configured to be mounted in at least one room, the wireless transceiver of each access point device being configured to broadcast to and receive radio frequency signals from the one or more optional monitoring devices, other access point devices within the room and the central hub access point device, wherein the transceivers within the access point devices measure a time of flight value of a radio signal sent between the one or more optional monitoring devices and the one or more access point devices optionally comprise software to use the measure of time of flight value to determine the distance between the one or more optional monitoring devices and each access point device and transmit a signal representing the distance data, and wherein the one or more access points are configured to transmit and receive signals between access points and measure a change in one or more of signal strength, link quality, or TOF of the transmitted signals and transmit a signal representing the measured change in one or more of signal strength, link quality, or TOF, whereby the change in signal strength, link quality or TOF are caused by multipath reflections and absorptions of the radio frequency signal off of the individual being monitored;

the central hub access point device being in communication with the one or more optional monitoring devices, the plurality of access point devices and the local computing device and configured to transmit data to the local computing device, wherein the central hub access point device is configured to receive the measure of time of flight value or distance from the one or more optional monitoring devices and change in one or more of signal strength, link quality, or TOF from the plurality of access point devices and to transmit the data received; and the local computing device is configured to be operated in the vicinity of the central hub access point device to receive from the central hub access point device the measure of time of flight value and change in one or more of signal strength, link quality, or TOF and is programmed with software configured to aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation, whereby the system has the capability to operate with or without the measure of time of flight value from the one or more optional monitoring devices such that the system has the capability of monitoring the location, movement and health of an individual whether or not the individual is wearing the monitoring device.

2. The system of claim 1, wherein the access point devices and the central hub access point device are configured to broadcast to and receive radio signals from other access point devices for automatically self-calibrating one or both of the location of the access point devices relative to each other within the room(s), and a parameter used to modify the distance calculation.

3. The system of claim 2, wherein the self calibration of the location of the access point devices and/or the parameter used to modify the distance calculation comprises one or both of a simultaneous localization and mapping (SLAM) algorithm and dual-Kalman filtering.

4. The system of claim 1, further comprising a remote computing device and a mobile computing device, wherein the local computing device is configured to transmit and the remote computing device is configured to receive data relating to one or more of the individual's 3-d position, velocity, acceleration, mobility, health status, activities of daily living, and determination of the individual experiencing an emergency situation, and wherein the remote computing device is configured to one or both of transmit health status and emergency alerts to the mobile computing device.

5. The system of claim 4, wherein one or both of the remote computing device and the local computing device is programmed with software using an algorithm that uses the measure of time of flight value to compute one or more of the position, velocity and acceleration of the individual within the facility.

6. The system of claim 5, wherein the algorithm used to estimate the position, velocity and acceleration of the individual within the environment is a sigma point Kalman filter, sigma-point Kalman smoother, sigma-point Kalman particle filter, or variant thereof.

7. The system of claim 1, wherein the local computing device comprises an algorithm to distinguish between activities related to an emergency situation and a non-emergency situation and is programmed with software that uses the analyzed data from the local computing device to do one or both of:
  cause alerts to be distributed to mobile computing devices of approved third-party entities when a probable emergency situation has occurred; and
  analyze and prepare data for use in continuously updated dashboards or reports that display on mobile devices of approved third-party entities,
  wherein the emergency and non-emergency events include one or more of falls, changes in gait, changes in average walking speed, changes in rooms visited during a period of time, and changes in activities of daily living including one or more of cooking, sleeping, sitting, eating, socializing, walking, entering or leaving a room, using a computer, going outside, going for a walk, going to the store, using the bathroom, going to a movie, or watching the television.

8. The system of claim 1, wherein the local computing device includes software programmed to receive data representing a floor-plan of the rooms and optionally the position of objects within the rooms that represents a digital representation of the rooms and optionally the position of objects within the room.

9. The system of claim 1, wherein the local computing device comprises software to control a procedure to calibrate position measurements with actual locations or way points within a room.

10. The system of claim 1, wherein the one or more optional monitoring devices include one or more of a 3-axis accelerometer, a 3-axis gyroscope, a barometric pressure sensor, a digital compass, and a global positioning system sensor for outdoor movement monitoring that are used for one or more of precise movement monitoring, walking speed, posture estimation, gait monitoring, and fall detection.

11. The system of claim 1, wherein the system is configured to operate with the measures of time of flight between one or more optional monitoring devices and one or more access points such that the system monitors and tracks individuals using data from the monitoring devices.

12. The system of claim 1, wherein the system is configured to operate without the measures of time of flight between one or more optional monitoring devices and one or more access points such that the system monitors and tracks individuals without using data from the monitoring devices.

13. The system of claim 12 wherein the local computing device is configured to calibrate the system using data from the monitoring devices at a first time such that the system can be used without the individuals wearing the monitoring devices at a second, later time.

14. The system of claim 1 wherein movement of the individual within a range of transmission of the one or more access point devices causes changes in one or more of the signal strength, the time of flight (TOF) and the link quality of the radio signals received by the access point devices, wherein the system is programmed with software to process a change in one or more of signal strength, TOF and link quality to determine the location of an individual within the room based on multipath reflections and absorption of the radio signal as it hits the individual moving through the facility and wherein the signal strength, link, and/or the TOF information measured by the access point devices and broadcast to the central hub access point device are used by the local computing device as inputs to an algorithm to determine the location of the individual within the facility.

15. The system of claim 1 wherein the one or more transceivers use one or both of chirp spread spectrum (CSS) and ultra wideband (UWB) as the method for estimating TOF.

16. The system of claim 1, wherein the local computing device is integrated into the central hub access point device.

17. The system of claim 1, wherein the monitoring device further comprises an emergency button or user interface that can be activated to transmit a signal to the local computing device that an emergency has occurred.

18. A method for using a system to monitor the location, movement and health of one or more individuals within an environment by a monitoring individual, the system comprising a plurality of access point devices in which each access point device includes at least one wireless transceiver, a central hub access point device including a wireless transceiver, a local computing device, and one or more optional monitoring devices including a wireless transceiver, the system having the capability of monitoring the location, movement and health of the one or more individuals with or without the monitoring devices being carried or worn upon the body of the individual, the method comprising the steps of:
  using the one or more optional monitoring devices carried or worn upon the body of the individual to measure a time of flight (TOF) value of a radio signal sent between the optional monitoring device and the at least one wireless transceiver located within each access point device;
  using the plurality of access point devices mounted in at least one room to one or both of measure a time of flight value of a radio signal sent between the one or more optional monitoring devices and access point devices and measure a change in one or more of signal strength, link quality, or TOF of the transmitted signals between access point devices;

receiving at the central hub access point device the measure of time of flight value from the one or more optional monitoring devices and change in one or more of signal strength, link quality, or TOF from the plurality of access point devices and transmitting the data received by the central hub access point device to the local computing device; and using the local computing device to receive from the central hub access point device the optional measure of time of flight value and the change in one or more of signal strength, link quality, or TOF and aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation, whereby the change in signal strength, link quality or TOF are caused by multipath reflections and absorptions of the radio frequency signal off of the individual being monitored; and whereby the system may be used with or without the measure of time of flight value from the one or more optional monitoring devices and whether or not the individual is wearing the monitoring device.

19. A system for monitoring the location, movement and health of one or more individuals within an environment by a monitoring individual, the system comprising a plurality of access point devices in which each access point device includes at least one wireless transceiver, a central hub access point device including a wireless transceiver, and a local computing device, wherein:

the plurality of access point devices being configured to be mounted in at least one room, the wireless transceiver of each access point device being configured to broadcast to and receive radio frequency signals from the other access points within the room and the central hub access point device, wherein the transceivers within the access point devices are configured to transmit and receive signals between access point devices and measure a change in one or more of signal strength, link quality, or TOF of the transmitted signals and transmit a signal representing the measured change in one or more of signal strength, link quality, or TOF, whereby the change in signal strength, link quality or TOF are caused by multipath reflections and absorptions of the radio frequency signal off of the individual being monitored;

the central hub access point device being in communication with the plurality of access point devices and the local computing device and configured to transmit data to the local computing device, wherein the central hub access point device is configured to receive the measure of change in one or more of signal strength, link quality, or TOF from the plurality of access point devices and to transmit the data received; and the local computing device being configured to be operated in the vicinity of the central hub access point device to receive from the central hub access point device the measure of change in one or more of signal strength, link quality, or TOF and is programmed with software configured to aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation.

20. A system for monitoring the location, movement and health of one or more individuals within an environment by a monitoring individual, the system comprising one or more monitoring devices including a wireless transceiver, a plurality of access point devices in which each access point device includes at least one wireless transceiver, a central hub access point device including a wireless transceiver, and a local computing device, wherein:

the one or more monitoring devices are configured to be carried or worn upon the body of the individual, the wireless transceiver of the monitoring device being configured to measure a time of flight value of a radio signal sent between the monitoring device and the at least one wireless transceiver located within at least one access point device, wherein the monitoring device comprises software programmed to use the measure of time of flight value to determine the distance between the monitoring device and the one or more access point devices and transmit a signal representing the distance that has been determined;

the one or more access point devices being configured to be mounted in at least one room, the wireless transceiver of each access point device being configured to broadcast to and receive radio frequency signals from the one or more monitoring devices, other access points within the room and the central hub access point device, wherein the transceivers within the access point devices that measure a time of flight value of a radio signal sent between the one or more monitoring devices and the one or more access point devices optionally comprise software to use the measure of time of flight value to determine the distance between the one or more monitoring devices and each access point device and to transmit a signal representing the distance data;

the central hub access point device being in communication with the one or more monitoring devices, the one or more access point devices and the local computing device and configured to transmit data to the local computing device, wherein the central hub access point device is configured to receive the measure of time of flight value from the one or more monitoring devices and to transmit the data received; and the local computing device is configured to be operated in the vicinity of the central hub access point device to receive from the central hub access point device the measure of time of flight value and is programmed with software configured to aggregate the data, optionally store the data on a storage medium, analyze the data using one or more algorithms programmed in the local computing device to track the individual's 3-d position, velocity and acceleration and assess mobility, and determine if the individual is experiencing an emergency situation, and provide a notification if there is an emergency situation, whereby the change in TOF are caused by multipath reflections and absorptions of the radio frequency signal off of the individual being monitored; and wherein the software of the local computing device is programmed with one or more of a sigma point Kalman filter algorithm, sigma-point Kalman smoother, sigma-point Kalman particle filter, or variant thereof that uses the measure of time of flight value measured between the monitoring device and the access points to compute one or both of the position, velocity and acceleration of the individual within the facility.

\* \* \* \* \*